United States Patent
Fujita et al.

(10) Patent No.: US 10,173,959 B2
(45) Date of Patent: Jan. 8, 2019

(54) LIQUID CRYSTAL COMPOSITION AND LIQUID CRYSTAL DISPLAY DEVICE

(75) Inventors: Yukihiro Fujita, Ichihara (JP); Yoshimasa Furusato, Ichihara (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 658 days.

(21) Appl. No.: 13/557,969

(22) Filed: Jul. 25, 2012

(65) Prior Publication Data

US 2013/0027654 A1 Jan. 31, 2013
US 2016/0244399 A9 Aug. 25, 2016

(30) Foreign Application Priority Data

Jul. 27, 2011 (JP) .................................. 2011-164298

(51) Int. Cl.

| | |
|---|---|
| *C09K 19/56* | (2006.01) |
| *C07C 69/52* | (2006.01) |
| *C09K 19/30* | (2006.01) |
| *C09K 19/44* | (2006.01) |
| *C09K 19/54* | (2006.01) |
| *C09K 19/02* | (2006.01) |
| *C09K 19/34* | (2006.01) |
| *G02F 1/1333* | (2006.01) |
| *C09K 19/04* | (2006.01) |
| *C09K 19/12* | (2006.01) |
| *G02F 1/137* | (2006.01) |

(52) U.S. Cl.
CPC .......... *C07C 69/52* (2013.01); *C09K 19/0208* (2013.01); *C09K 19/3066* (2013.01); *C09K 19/3068* (2013.01); *C09K 19/3402* (2013.01); *C09K 19/44* (2013.01); *C09K 19/54* (2013.01); *C09K 19/542* (2013.01); *G02F 1/133365* (2013.01); *C09K 2019/0448* (2013.01); *C09K 2019/122* (2013.01); *C09K 2019/123* (2013.01); *C09K 2019/3015* (2013.01); *C09K 2019/3043* (2013.01); *C09K 2019/3071* (2013.01); *C09K 2019/3078* (2013.01); *C09K 2019/3422* (2013.01); *C09K 2019/3425* (2013.01); *C09K 2019/548* (2013.01); *G02F 2001/13706* (2013.01); *G02F 2001/13712* (2013.01); *Y10T 428/10* (2015.01)

(58) Field of Classification Search
CPC .... C09K 19/3066; C09K 19/44; C09K 19/54; C09K 2019/122; C09K 2019/123; C09K 2019/2043; B32B 2457/20; B32B 2457/202; G02F 2001/133633; G02F 2001/133765; G02F 2001/13712; G02F 2001/13775; C07C 69/34; C07C 69/52; C07C 69/604

USPC ................ 428/1.1; 349/182, 191; 252/299.4, 252/299.5; 560/190

See application file for complete search history.

(56) References Cited

U.S. PATENT DOCUMENTS

| | | | |
|---|---|---|---|
| 6,256,082 B1 * | 7/2001 | Suzuki .............. | G02F 1/133753 349/117 |
| 2004/0011996 A1 | 1/2004 | Klasen-Memmer et al. | |
| 2009/0065739 A1 * | 3/2009 | Haseba .............. | C09K 19/0275 252/299.62 |
| 2009/0103011 A1 | 4/2009 | Bernatz et al. | |
| 2009/0141215 A1 | 6/2009 | Bremer et al. | |
| 2010/0304049 A1 | 12/2010 | Bernatz et al. | |
| 2011/0101269 A1 | 5/2011 | Bernatz et al. | |
| 2011/0242473 A1 * | 10/2011 | Haseba et al. ................. | 349/139 |

FOREIGN PATENT DOCUMENTS

| | | |
|---|---|---|
| CN | 101045866 | 4/2007 |
| WO | 2009/030318 A | 3/2009 |
| WO | 2009/030322 A | 3/2009 |
| WO | WO 2010058681 A1 * | 5/2010 |

* cited by examiner

*Primary Examiner* — Ruiyun Zhang
(74) *Attorney, Agent, or Firm* — Hogan Lovells US LLP

(57) ABSTRACT

To provide a liquid crystal composition satisfying at least one characteristic such as a high maximum temperature of a nematic phase, a low minimum temperature thereof, a small viscosity, a suitable optical anisotropy, a large negative dielectric anisotropy, a large specific resistance, a high stability to ultraviolet light and heat, or a liquid crystal composition having a suitable balance regarding at least two characteristics, and an AM device having a short response time, a large voltage holding ratio, a large contrast ratio and a long service life; a liquid crystal composition contains a specific compound having a polymerizable group as a first component, and may contain a specific compound having a large negative dielectric anisotropy and a low minimum temperature as a second component or a specific compound having a small viscosity or a large maximum temperature as a third component, and a liquid crystal display device contains the composition.

14 Claims, No Drawings

LIQUID CRYSTAL COMPOSITION AND LIQUID CRYSTAL DISPLAY DEVICE

This is a Non-Provisional application, which claims priority to Japanese Patent Application No. 2011-164298 filed on Jul. 27, 2011; the contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The invention relates to a liquid crystal composition containing a polymerizable compound that is polymerized, for example, by light or heat. The invention also relates to a liquid crystal display device in which the liquid crystal composition is sealed between substrates, and the polymerizable compound contained in the liquid crystal composition is polymerized while adjusting a voltage applied to a liquid crystal layer to immobilize alignment of liquid crystals.

As the technical field, the invention relates to a liquid crystal composition mainly suitable for use in an active matrix (AM) device and so forth, and an AM device and so forth containing the composition. More specifically, the invention relates to a liquid crystal composition having a negative dielectric anisotropy, and a device and so forth that contain the composition and have a mode such as an in-plane switching (IPS) mode, a vertical alignment (VA) mode or a polymer sustained alignment (PSA) mode. The VA mode includes a multi-domain vertical alignment (MVA) mode and a patterned vertical alignment (PVA) mode.

BACKGROUND ART

In a liquid crystal display device, a classification based on an operating mode for liquid crystals includes a phase change (PC) mode, a twisted nematic (TN) mode, a super twisted nematic (STN) mode, an electrically controlled birefringence (ECB) mode, an optically compensated bend (OCB) mode, an in-plane switching (IPS) mode, a vertical alignment (VA) mode and a polymer sustained alignment (PSA) mode. A classification based on a driving mode in the device includes a passive matrix (PM) and an active matrix (AM). The PM is further classified into static, multiplex and so forth, and the AM is classified into a thin film transistor (TFT), a metal insulator metal (MIM) and so forth. The TFT is further classified into amorphous silicon and polycrystal silicon. The latter is classified into a high temperature type and a low temperature type according to a production process. A classification based on a light source includes a reflective type utilizing natural light, a transmissive type utilizing backlight and a transflective type utilizing both the natural light and the backlight.

The devices contain a liquid crystal composition having suitable characteristics. The liquid crystal composition has a nematic phase. General characteristics of the composition should be improved to obtain an AM device having good general characteristics. Table 1 below summarizes a relationship of the general characteristics between two aspects. The general characteristics of the composition will be further explained based on a commercially available AM device. A temperature range of the nematic phase relates to a temperature range in which the device can be used. A preferred maximum temperature of the nematic phase is approximately 70° C. or higher and a preferred minimum temperature of the nematic phase is approximately −10° C. or lower. Viscosity of the composition relates to a response time in the device. A short response time is preferred for displaying moving images on the device. Accordingly, a small viscosity in the composition is preferred. A small viscosity at a low temperature is further preferred.

TABLE 1

General Characteristics of Composition and AM Device

| No. | General Characteristics of Composition | General Characteristics of AM Device |
|---|---|---|
| 1 | Wide temperature range of a nematic phase | Wide usable temperature range |
| 2 | Small viscosity[1] | Short response time |
| 3 | Suitable optical anisotropy | Large contrast ratio |
| 4 | Large positive or negative dielectric anisotropy | Low threshold voltage and small electric power consumption Large contrast ratio |
| 5 | Large specific resistance | Large voltage holding ratio and large contrast ratio |
| 6 | High stability to ultraviolet light and heat | Long service life |

[1]A liquid crystal composition can be injected into a liquid crystal cell in a shorter period of An optical anisotropy of the composition relates to a contrast ratio in the device. A product (Δn×d) of the optical anisotropy (Δn) of the composition and a cell gap (d) in the device is designed so as to maximize the contrast ratio. A suitable value of the product depends on the type of the operating mode. The suitable value is in the range of approximately 0.30 micrometer to approximately 0.40 micrometer in a device having the VA mode or the PSA mode, and in the range of approximately 0.20 micrometer to approximately 0.30 micrometer in a device having the IPS mode. In the above case, a composition having a large optical anisotropy is preferred for a device having a small cell gap. A large absolute value of a dielectric anisotropy in the composition contributes to a low threshold voltage, a small electric power consumption and a large contrast ratio in the device. Accordingly, the large absolute value of the dielectric anisotropy is preferred. A large specific resistance in the composition contributes to a large voltage holding ratio and a large contrast ratio in the device. Accordingly, a composition having a large specific resistance at room temperature and also at a high temperature in an initial stage is preferred. A composition having a large specific resistance at room temperature and also at a high temperature even after the device has been used for a long period of time is preferred. Stability of the composition to ultraviolet light and heat relates to a service life of the liquid crystal display device. In the case where the stability is high, the device has a long service life. Such characteristics are preferred for an AM device used in a liquid crystal projector, a liquid crystal television and so forth.

A composition having a positive dielectric anisotropy is used for an AM device having the TN mode. On the other hand, a composition having a negative dielectric anisotropy is used for an AM device having the VA mode. A composition having a positive or negative dielectric anisotropy is used for an AM device having the IPS mode. A composition having a positive or negative dielectric anisotropy is used for an AM device having the PSA mode. Examples of the liquid crystal composition having the negative dielectric anisotropy are disclosed in Patent literatures No. 1 to No. 6 as described below and so forth.

CITATION LIST

Patent Literature

Patent literature No. 1: JP 2004-131704 A.
Patent literature No. 2: JP 2009-102639 A.
Patent literature No. 3: WO 2009/030318 A.
Patent literature No. 4: WO 2009/030322 A.
Patent literature No. 5: CN 101045866 A.
Patent literature No. 6: JP 2009-132718 A.

A desirable AM device has characteristics such as a wide temperature range in which a device can be used, a short response time, a large contrast ratio, a low threshold voltage, a large voltage holding ratio and a long service life. A shorter response time even by one millisecond is desirable. Thus, desirable characteristics of a composition include a high maximum temperature of a nematic phase, a low minimum temperature of the nematic phase, a small viscosity, a suitable optical anisotropy, a large positive or negative dielectric anisotropy, a large specific resistance, a high stability to ultraviolet light and a high stability to heat.

In a display having a PSA mode, a small amount (approximately 0.3% by weight to approximately 1% by weight) of a polymerizable compound (RM) is added to a liquid crystal composition. After introduction into a liquid crystal display cell, only the polymerizable compound is polymerized ordinarily under irradiation with ultraviolet light in a state in which a voltage is applied between electrodes to form a polymer structure within the device. As the RM, a polymerizable mesogenic or liquid crystal compound is known to be particularly suitable as a monomer to be added to the liquid crystal composition.

SUMMARY OF INVENTION

The inventors of the invention have diligently continued to conduct research for solving the problem, as a result, have found that a specific liquid crystal composition satisfies desirable characteristics and a liquid crystal display device containing the composition exhibits an excellent performance, and thus has completed the invention based on the knowledge.

The invention concerns a liquid crystal composition containing at least one compound selected from the group of specific compounds as a first component.

The invention also concerns a liquid crystal display device, comprising two substrates having an electrode layer on at least one of the substrates, and arranging the liquid crystal composition between the two substrates.

The invention further concerns use of the liquid crystal composition in the liquid crystal display device.

Technical Problem

In general, the polymerizable mesogenic or liquid crystal compound described above has a high capability of aligning liquid crystal molecules. On the other hand, the compound has a poor solubility in a liquid crystal composition, and crystallization during transportation or in a liquid crystal display device is concerned. Meanwhile, use of a polymerizable compound (RM) in a larger amount has been required from a demand for improving characteristics of the liquid crystal composition in recent years.

One of the aims of the invention is to apply a non-mesogen polymerizable compound that is believed to have a high solubility in the liquid crystal composition as a monomer to be added to the liquid crystal composition. Another aim of the invention is to provide a liquid crystal composition satisfying at least one of characteristics such as a high maximum temperature of a nematic phase, a low minimum temperature of the nematic phase, a small viscosity, a suitable optical anisotropy, a large negative dielectric anisotropy, a large specific resistance, a high stability to ultraviolet light and a high stability to heat. A further aim is to provide a liquid crystal composition having a suitable balance regarding at least two of the characteristics. A still further aim is to provide a liquid crystal display device containing such a composition. An additional aim is to provide a composition having a suitable optical anisotropy to be a small optical anisotropy or a large optical anisotropy, a large negative dielectric anisotropy and a high stability to ultraviolet light, and is to provide an AM device having a short response time, a large voltage holding ratio, a large contrast ratio, a long service life and so forth.

Solution to Problem

The invention concerns a liquid crystal composition containing at least one compound selected from the group of compounds represented by formula (1) as a first component, and a liquid crystal display device containing the composition:

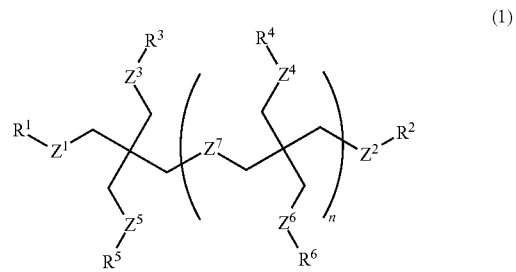

wherein $R^1$, $R^2$, $R^3$, $R^4$, $R^5$ and $R^6$ are independently hydrogen, halogen, hydroxy, —$CH_2OH$, —$SF_5$, —$NO_2$, P-Sp- or alkyl having 1 to 30 carbons, the alkyl is straight-chain, branched-chain or cyclic, the alkyl may have an unsaturated bond, and in the alkyl, at least one of non-adjacent —$CH_2$— may be replaced by —O—, —S—, —CO—, —CO—O— or —O—CO—, and in the groups, at least one of hydrogen may be replaced by halogen; P is a polymerizable group; Sp is a single bond or alkylene having 1 to 20 carbons, and in the alkylene, at least one of hydrogen may be replaced by halogen or —C≡N, and in the groups, at least one of non-adjacent —$CH_2$— may be independently replaced by —O—, —S—, —NH—, —$NR^7$—, —$SiR^7R^8$—, —CO—, —COO—, —OCO—, —OCO—O—, —S—CO—, —CO—S—, —$NR^7$—CO—O—, —O—CO—$NR^7$—, —$NR^7$—CO—$NR^8$—, —CH=CH— or —C≡C—; at least one of $R^1$, $R^2$, $R^3$, $R^4$, $R^5$ and $R^6$ is P-Sp-; $Z^1$, $Z^2$, $Z^3$, $Z^4$, $Z^5$ and $Z^6$ are independently a single bond, —O—, —S—, —CO—, —CO—O—, —O—CO—, —O—CO—O— or alkylene having 1 to 12 carbons; $Z^7$ is independently —O—, —S—, —CO—, —CO—O—, —O—CO—, —O—CO—O—, —$OCH_2$—, —$CH_2O$—, —$SCH_2$—, —$CH_2S$—, —$CF_2O$—, —$OCF_2$—, —$CF_2S$—, —$SCF_2$—, —$(CR^7R^8)_m$—, —$(CR^7=CR^8)_m$—, —C≡C—, —CR$^7$=CR$^8$—CO—O—, —O—CO—CR$^7$=CR$^8$—, —CO—NR$^7$—, —NR$^7$—CO—, —CO—S—, —S—CO—, —O—CO—CR$^7$—CR$^8$—O—, —O—CR$^7$—CR$^8$—CO—O—, —CR$^7$=CR$^8$—CO—, —CO—CR$^7$=CR$^8$—, —C(=CR$^7$R$^8$)—, —O—CO—CR$^7$R$^8$—CR$^9$R$^{10}$—O—, —O—CR$^7$R$^8$—CR$^9$R$^{10}$—CO—O— or a single bond; R$^7$, R$^8$, R$^9$ and R$^{10}$ are independently hydrogen, halogen or alkyl having 1 to 12 carbons, the alkyl is straight-chain, branched-chain or cyclic, the alkyl may have an unsaturated bond, and in the alkyl, at least one of non-adjacent —CH$_2$— may be replaced by —O—, —S—, —CO—, —CO—O— or —O—CO—, and in the groups, at least one of hydrogen may be replaced by halogen; m is 1, 2, 3 or 4; and n is an integer from 1 to 12.

Advantageous Effects of Invention

An advantage of the invention is a high solubility of a polymerizable compound in a liquid crystal composition. Another advantage of the invention is a liquid crystal composition satisfying at least one of characteristics such as a high maximum temperature of a nematic phase, a low minimum temperature of the nematic phase, a small viscosity, a suitable optical anisotropy, a large negative dielectric anisotropy, a large specific resistance, a high stability to ultraviolet light and a high stability to heat. One aspect of the invention is a liquid crystal composition having a suitable balance regarding at least two of the characteristics. Another aspect is a liquid crystal display device containing such a composition. A further aspect is a polymerizable compound having a high solubility, a composition having a suitable optical anisotropy, a large negative dielectric anisotropy, a high stability to ultraviolet light and so forth, and an AM device having a short response time, a large voltage holding ratio, a large contrast ratio, a long service life and so forth.

DESCRIPTION OF EMBODIMENTS

Usage of terms in the specification and claims is as described below. A liquid crystal composition or a liquid crystal display device of the invention may be abbreviated as "composition" or "device," respectively. The liquid crystal display device is a generic term for a liquid crystal display panel and a liquid crystal display module. "Liquid crystal compound" means a compound having a liquid crystal phase such as a nematic phase or a smectic phase, or a compound having no liquid crystal phase but being useful as a component of the composition. The useful compound has a six-membered ring such as 1,4-cyclohexylene and 1,4-phenylene, and a rod like molecular structure. An optically active compound and a polymerizable compound may occasionally be added to the composition. Even in the case where the compounds are liquid crystalline, the compounds are classified as an additive herein. At least one compound selected from the group of compounds represented by formula (1) may be abbreviated as "compound (1)." "Compound (1)" means one compound or two or more compounds represented by formula (1). A same rule applies to any other compound represented by any other formula. "At least one" to be "replaced" indicates any of not only positions but also numbers.

A higher limit of a temperature range of the nematic phase may be abbreviated as "maximum temperature." A lower limit of the temperature range of the nematic phase may be abbreviated as "minimum temperature." An expression "having a specific resistance" means that the composition has a large specific resistance at room temperature and also at a temperature close to the maximum temperature of the nematic phase in an initial stage, and that the composition has a large specific resistance at room temperature and also at a temperature close to the maximum temperature of the nematic phase even after the device has been used for a long period of time. An expression "having a large voltage holding ratio" means that the device has a large voltage holding ratio at room temperature and also at a high temperature in an initial stage, and that the device has a large voltage holding ratio at room temperature and also at a temperature close to the maximum temperature of the nematic phase even after the device has been used for a long period of time. When characteristics such as an optical anisotropy are explained, values obtained according to the measuring methods described in Examples will be used. A first component includes one compound or two or more compounds. "Ratio of the first component" is expressed in terms of a weight ratio (part by weight) of the first component based on 100 parts by weight of a liquid crystal composition excluding the first component. "Ratio of a second component" is expressed in terms of weight percent (% by weight) of the second component based on the weight of the liquid crystal composition excluding the first component. "Ratio of a third component" is expressed in a manner similar to "ratio of the second component." A ratio of the additive mixed with the composition is expressed in terms of weight percent (% by weight) or weight parts per million (ppm) based on the total weight of the liquid crystal composition.

A symbol R$^{11}$ is used for a plurality of compounds in chemical formulas of component compounds. A group to be selected by R$^{11}$ may be identical or different in two of arbitrary compounds among the plurality of compounds. In one case, for example, R$^{11}$ of compound (2-1) is ethyl and R$^{11}$ of compound (2-2) is ethyl. In another case, R$^{11}$ of compound (2-1) is ethyl and R$^{11}$ of compound (2-2) is propyl. A same rule applies to a symbol R$^1$, X$^1$ or the like. The invention includes the items described below.

Item 1. A liquid crystal composition containing at least one compound selected from the group of compounds represented by formula (1) as a first component:

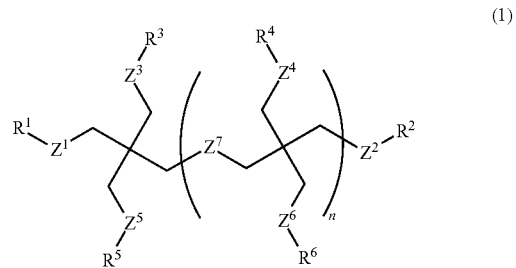

(1)

wherein R$^1$, R$^2$, R$^3$, R$^4$, R$^5$ and R$^6$ are independently hydrogen, halogen, hydroxy, —CH$_2$OH, —SF$_5$, —NO$_2$, P-Sp- or alkyl having 1 to 30 carbons, the alkyl is straight-chain, branched-chain or cyclic, the alkyl may have an unsaturated bond, and in the alkyl, at least one of non-adjacent —CH$_2$— may be replaced by —O—, —S—, —CO—, —CO—O— or —O—CO—, and in the groups, at least one of hydrogen may be replaced by halogen; P is a polymerizable group; Sp is a single bond or alkylene having 1 to 20 carbons, and in the alkylene, at least one of hydrogen may be replaced by halogen or —CN, and in the groups, at least one of non-adjacent —CH$_2$— may be independently replaced by —O—, —S—, —NH—, —NR$^7$—, —SiR$^7$R$^8$—, —CO—, —COO—, —OCO—, —OCO—O—, —S—CO—, —CO—S—, —NR$^7$—CO—O—, —O—CO—NR$^7$—, —NR$^7$—CO—NR$^8$—, —CH=CH— or —C≡C—; at least one of R$^1$, R$^2$, R$^3$, R$^4$, R$^5$ and R$^6$ is P-Sp-; Z$^2$, Z$^2$, Z$^3$, Z$^4$, Z$^5$ and Z$^6$ are independently a single bond, —O—, —S—, —CO—, —CO—O—, —O—CO—, —O—CO—O— or alkylene having 1 to 12 carbons; Z$^7$ is independently —O—, —S—, —CO—, —CO—O—, —O—CO—, —O—CO—O—, —OCH$_2$—, —CH$_2$O—, —SCH$_2$—, —CH$_2$S—, —CF$_2$O—, —OCF$_2$—, —CF$_2$S—, —SCF$_2$—, —(CR$^7$R$^8$)$_m$—, —(CR$^7$=CR$^8$)$_m$—, —C≡C—, —CR$^7$=CR$^8$—CO—O—, —O—CO—CR$^7$=CR$^8$—, —CO—NR$^7$—, —NR$^7$—CO—, —CO—S—, —S—CO—, —O—CO—CR$^7$=CR$^8$—O—, —O—CR$^7$=CR$^8$—CO—O—, —CR$^7$=CR$^8$—CO—, —CO—CR$^7$=CR$^8$—, —C(=CR$^7$R$^8$)—, —O—CO—CR$^7$R$^8$—CR$^9$R$^{10}$—O—, —O—CR$^7$R$^8$—CR$^9$R$^{10}$—CO—O or a single bond; R$^7$, R$^8$, R$^9$ and R$^{10}$ are independently hydrogen, halogen or alkyl having 1 to 12 carbons, the alkyl is straight-chain, branched-chain or cyclic, the alkyl may have an unsaturated bond, and in the alkyl, at least one of non-adjacent —CH$_2$— may be replaced by —O—, —S—, —CO—, —CO—O— or —O—CO—, and in the groups, at least one of hydrogen may be replaced by halogen; m is 1, 2, 3 or 4; and n is an integer from 1 to 12.

Item 2. The liquid crystal composition according to item 1, wherein, in formula (1), R$^1$, R$^2$, R$^3$, R$^4$, R$^5$ and R$^6$ are independently hydrogen, hydroxy, alkyl having 1 to 12 carbons, alkoxy having 1 to 12 carbons, alkenyl having 2 to 12 carbons, alkenyl having 2 to 12 carbons in which at least one of hydrogen is replaced by fluorine, or a group selected from the group of groups represented by formula (P-1) to formula (P-9); and at least one of R$^1$, R$^2$, R$^3$, R$^4$, R$^5$ and R$^6$ is a group selected from the group of groups represented by formula (P-1) to formula (P-9):

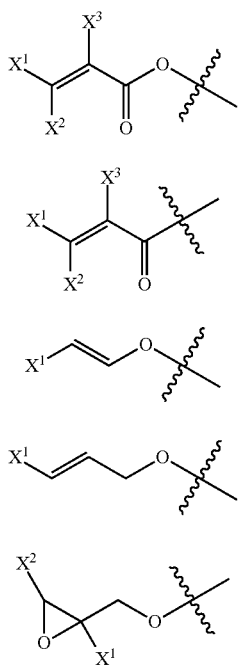

(P-1)

(P-2)

(P-3)

(P-4)

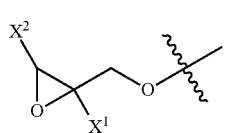

(P-5)

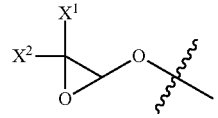

(P-6)

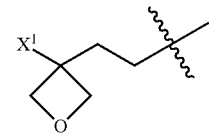

(P-7)

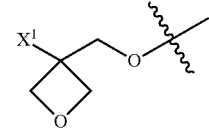

(P-8)

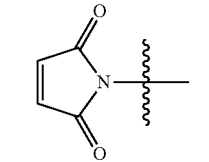

(P-9)

wherein X$^2$ and X$^2$ are independently hydrogen, —CH$_3$, —C$_2$H$_5$ or halogen; and X$^3$ is hydrogen, —CH$_3$, —C$_2$H$_5$, halogen or —CF$_3$.

Item 3. The liquid crystal composition according to item 1, wherein the first component is at least one compound selected from the group of compounds represented by formula (1-1) to formula (1-2):

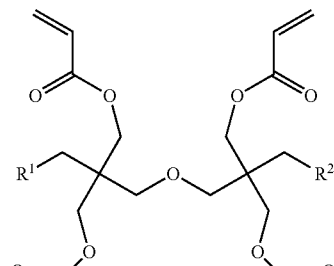

(1-1)

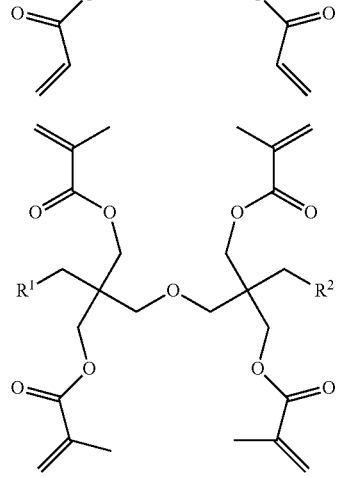

(1-2)

wherein R$^1$ and R$^2$ are independently hydrogen, halogen, hydroxy, —CH$_2$OH, —SF$_5$, —NO$_2$, P— or alkyl having 1 to 12 carbons, the alkyl is straight-chain, branched-chain or cyclic, the alkyl may have an unsaturated bond, and in the alkyl, at least one of non-adjacent —$CH_2$— may be replaced by —O—, —S—, —CO—, —CO—O— or —O—CO—, and in the groups, at least one of hydrogen may be replaced by halogen; and P is acryloyloxy or methacryloyloxy.

Item 4. The liquid crystal composition according to any one of items 1 to 3, wherein a ratio of the first component is in the range of 0.05 part by weight to 10 parts by weight based on 100 parts by weight of a liquid crystal composition excluding the first component.

Item 5. The liquid crystal composition according to any one of items 1 to 4, further containing at least one compound selected from the group of compounds represented by formula (2) as a second component:

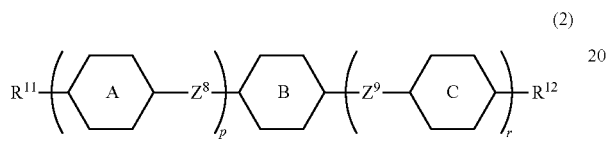

(2)

wherein $R^{11}$ and $R^{12}$ are independently alkyl having 1 to 12 carbons, alkoxy having 1 to 12 carbons or alkenyl having 2 to 12 carbons, or alkenyl having 2 to 12 carbons in which at least one of hydrogen is replaced by fluorine; ring A and ring C are independently 1,4-cyclohexylene, 1,4-phenylene, 1,4-phenylene in which at least one of hydrogen is replaced by fluorine or chlorine, or tetrahydropyran-2,5-diyl; ring B is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl; $Z^8$ and $Z^9$ are independently a single bond, ethylene, methyleneoxy or carbonyloxy; p is 1, 2 or 3; r is 0 or 1; and a sum of p and r is 3 or less.

Item 6. The liquid crystal composition according to item 5, wherein the second component is at least one compound selected from the group of compounds represented by formula (2-1) to formula (2-19):

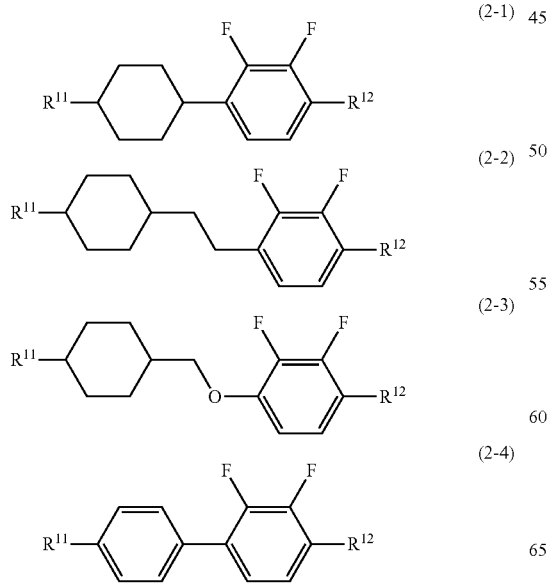

(2-1)
(2-2)
(2-3)
(2-4)

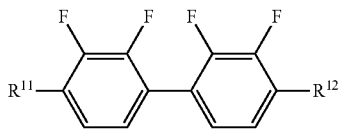

(2-5)

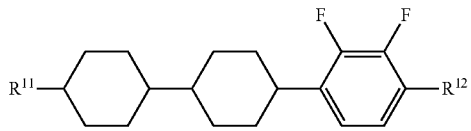

(2-6)

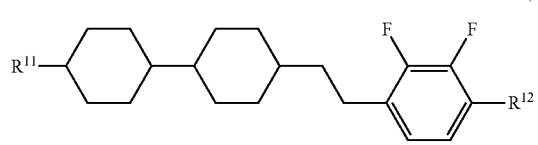

(2-7)

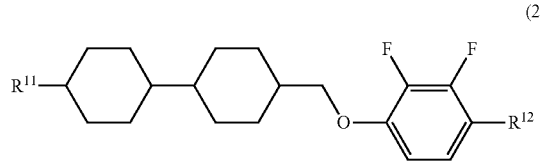

(2-8)

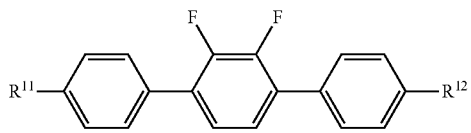

(2-9)

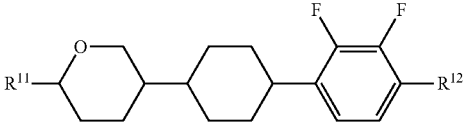

(2-10)

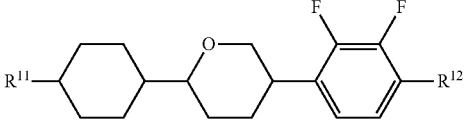

(2-11)

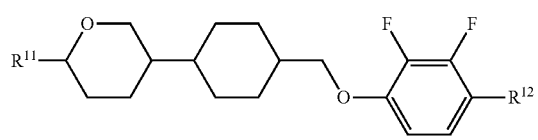

(2-12)

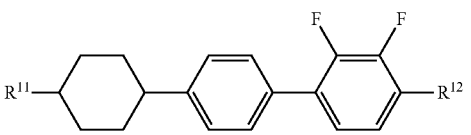

(2-13)

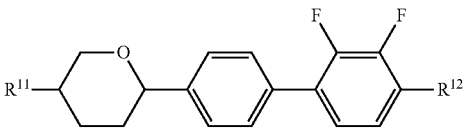

(2-14)

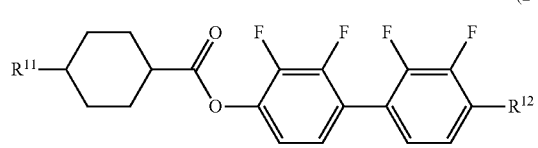

(2-15)

-continued (2-16)
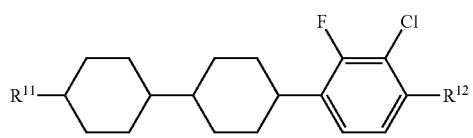

(2-17)
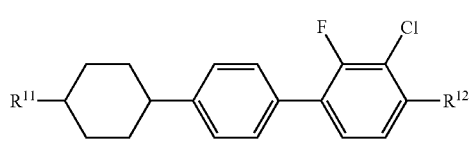

(2-18)
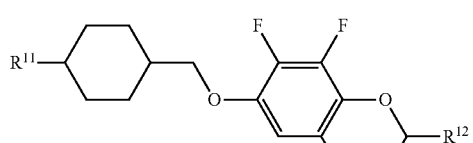

(2-19)
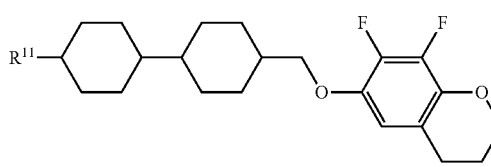

wherein $R^{11}$ and $R^{12}$ are independently alkyl having 1 to 12 carbons, alkoxy having 1 to 12 carbons or alkenyl having 2 to 12 carbons, or alkenyl having 2 to 12 carbons in which at least one of hydrogen is replaced by fluorine.

Item 7. The liquid crystal composition according to item 5, wherein the second component is at least one compound selected from the group of compounds represented by formula (2-1) according to item 6.

Item 8. The liquid crystal composition according to item 5, wherein the second component is a mixture of at least one compound selected from the group of compounds represented by formula (2-1) and at least one compound selected from the group of compounds represented by formula (2-6) according to item 6.

Item 9. The liquid crystal composition according to item 5, wherein the second component is a mixture of at least one compound selected from the group of compounds represented by formula (2-1) and at least one compound selected from the group of compounds represented by formula (2-13) according to item 6.

Item 10. The liquid crystal composition according to item 5, wherein the second component is a mixture of at least one compound selected from the group of compounds represented by formula (2-4) and at least one compound selected from the group of compounds represented by formula (2-8) according to item 6.

Item 11. The liquid crystal composition according to any one of items 5 to 10, wherein a ratio of the second component is in the range of 10% by weight to 90% by weight based on the weight of a liquid crystal composition excluding the first component.

Item 12. The liquid crystal composition according to any one of items 1 to 11, further containing at least one compound selected from the group of compounds represented by formula (3) as a third component:

(3)
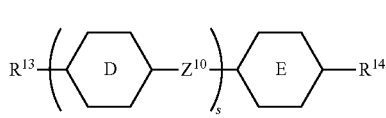

wherein $R^{13}$ and $R^{14}$ are independently alkyl having 1 to 12 carbons, alkoxy having 1 to 12 carbons or alkenyl having 2 to 12 carbons, or alkenyl having 2 to 12 carbons in which at least one of hydrogen is replaced by fluorine; ring D and ring E are independently 1,4-cyclohexylene, 1,4-phenylene, 2-fluoro-1,4-phenylene, 3-fluoro-1,4-phenylene or 2,5-difluoro-1,4-phenylene; $Z^{10}$ is independently a single bond, ethylene, methyleneoxy or carbonyloxy; and s is 1, 2 or 3.

Item 13. The liquid crystal composition according to item 12, wherein the third component is at least one compound selected from the group of compounds represented by formula (3-1) to formula (3-13):

(3-1)
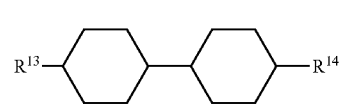

(3-2)
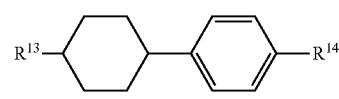

(3-3)
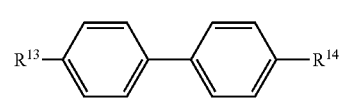

(3-4)
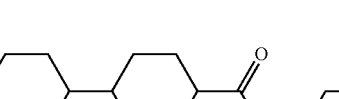

(3-5)
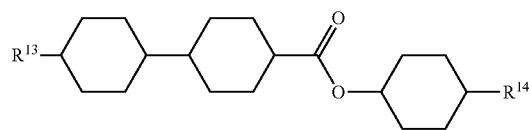

(3-6)
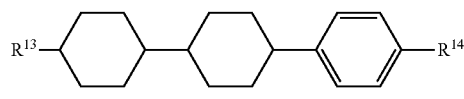

(3-7)
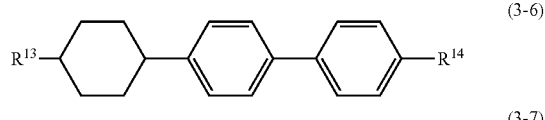

(3-8)
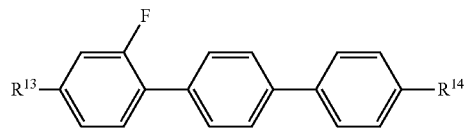

(3-9)
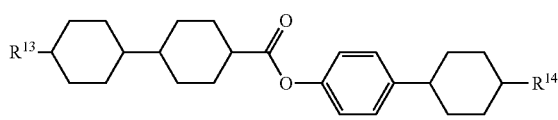

(3-10)

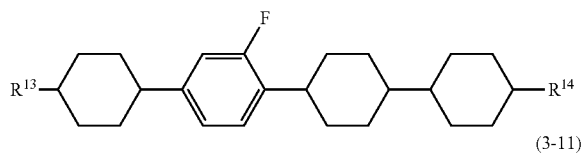

(3-11)

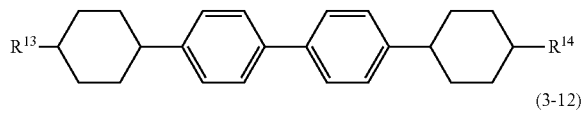

(3-12)

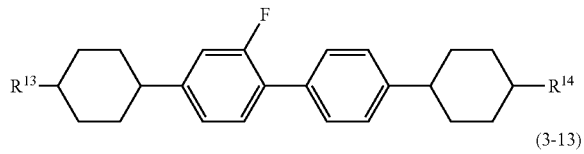

(3-13)

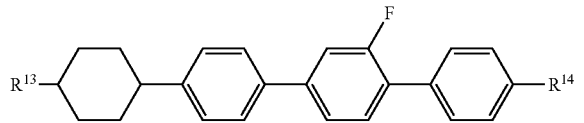

wherein $R^{13}$ and $R^{14}$ are independently alkyl having 1 to 12 carbons, alkoxy having 1 to 12 carbons or alkenyl having 2 to 12 carbons, or alkenyl having 2 to 12 carbons in which at least one of hydrogen is replaced by fluorine.

Item 14. The liquid crystal composition according to item 12, wherein the third component is at least one compound selected from the group of compounds represented by formula (3-1) according to item 13.

Item 15. The liquid crystal composition according to item 12, wherein the third component is a mixture of at least one compound selected from the group of compounds represented by formula (3-1) and at least one compound selected from the group of compounds represented by formula (3-5) according to item 13.

Item 16. The liquid crystal composition according to item 12, wherein the third component is a mixture of at least one compound selected from the group of compounds represented by formula (3-1) and at least one compound selected from the group of compounds represented by formula (3-7) according to item 13.

Item 17. The liquid crystal composition according to item 12, wherein the third component is a mixture of at least one compound selected from the group of compounds represented by formula (3-1), at least one compound selected from the group of compounds represented by formula (3-5) and at least one compound selected from the group of compounds represented by formula (3-7) according to item 13.

Item 18. The liquid crystal composition according to any one of items 12 to 17, wherein a ratio of the third component is in the range of 10% by weight to 90% by weight based on the weight of a liquid crystal composition excluding the first component.

Item 19. The liquid crystal composition according to any one of items 1 to 18, further containing a polymerization initiator.

Item 20. The liquid crystal composition according to any one of items 1 to 19, further containing a polymerization inhibitor.

Item 21. The liquid crystal composition according to any one of items 1 to 20, wherein a maximum temperature of a nematic phase is 70° C. or higher, an optical anisotropy (25° C.) at a wavelength of 589 nanometers is 0.08 or more, and a dielectric anisotropy (25° C.) at a frequency of 1 kHz is −2 or less.

Item 22. A liquid crystal display device, comprising two substrates having an electrode layer on at least one of the substrates, and arranging the liquid crystal composition according to any one of items 1 to 21 between the two substrates.

Item 23. The liquid crystal display device according to item 22, wherein an operating mode in the liquid crystal display device is a TN mode, a VA mode, an IPS mode or a PSA mode, and a driving mode in the liquid crystal display device is an active matrix mode.

Item 24. Use of the liquid crystal composition according to any one of items 1 to 21 in the liquid crystal display device.

The invention further includes the following items: (1) the composition, further containing the optically active compound; (2) the composition, further containing the additive such as an antioxidant, an ultraviolet light absorber or an antifoaming agent; (3) an AM device containing the composition; (4) a device containing the composition, and having a TN, ECB, OCB, IPS, VA or PSA mode; (5) a transmissive device, containing the composition; (6) use of the composition as the composition having the nematic phase; and (7) use as an optically active composition by adding the optically active compound to the composition.

The composition of the invention will be explained in the following order. First, a constitution of the component compounds in the composition will be explained. Second, main characteristics of the component compounds and main effects of the compounds on the composition will be explained. Third, a combination of components in the composition, a preferred ratio of the components and the basis thereof will be explained. Fourth, a preferred embodiment of the component compounds will be explained. Fifth, specific examples of the component compounds will be shown. Sixth, the additive that may be mixed with the composition will be explained. Seventh, methods for synthesizing the component compounds will be explained. Last, an application of the composition will be explained.

First, the constitution of the component compounds in the composition will be explained. The composition of the invention is classified into composition A and composition B. Composition A may further contain any other liquid crystal compound, the additive and an impurity, in addition to the liquid crystal compound selected from compound (1), compound (2) and compound (3). "Any other liquid crystal compound" means a liquid crystal compound different from compound (1), compound (2) and compound (3). Such a compound is mixed with the composition for the purpose of further adjusting the characteristics. Of any other liquid crystal compounds, a ratio of a cyano compound is preferably as small as possible in view of stability to heat or ultraviolet light. A further preferred ratio of the cyano compound is 0% by weight. The additive includes the optically active compound, the antioxidant, the ultraviolet light absorber, a dye, the antifoaming agent and the polymerization initiator. The impurity includes a compound mixed in a process such as preparation of the component compounds. Even in the case where the compound is liquid crystalline, the compound is classified as the impurity herein.

Composition B consists essentially of compound (1), compound (2) and compound (3). A term "essentially" means that the composition may also contain the additive and the impurity, but does not contain any liquid crystal compound different from the compounds. Composition B has a smaller number of components than composition A has. Composition B is preferred to composition A in view of cost reduction. Composition A is preferred to composition B in view of possibility of further adjusting physical properties by mixing any other liquid crystal compound.

Second, the main characteristics of the component compounds and the main effects of the compounds on the characteristics of the composition will be explained. The main characteristics of the component compounds are summarized in Table 2 on the basis of advantageous effects of the invention. In Table 2, a symbol L stands for "large" or "high," a symbol M stands for "medium," and a symbol S stands for "small" or "low." The symbols L, M and S represent a classification based on a qualitative comparison among the component compounds, and 0 (zero) means "a value is close to zero."

TABLE 2

Characteristics of Compounds

| Compounds | Compound (2) | Compound (3) |
|---|---|---|
| Maximum Temperature | S to L | S to L |
| Viscosity | M to L | S to M |
| Optical Anisotropy | M to L | S to L |
| Dielectric Anisotropy | M to L[1)] | 0 |
| Specific Resistance | L | L |

[1)]A value of the dielectric anisotropy is negative, and the symbol shows magnitude of an absolute value.

Upon mixing the component compounds with the composition, the main effects of the component compounds on the characteristics of the composition are as described below. Compound (2) increases the absolute value of the dielectric anisotropy, and decreases the minimum temperature. Compound (3) decreases the viscosity, or increases the maximum temperature.

Third, the combination of components in the composition, the preferred ratio of the components and the basis thereof will be explained. The combination of the components in the composition includes a combination of the first component and the second component, and a combination of the first component, the second component and the third component.

A preferred ratio of the first compound is approximately 0.05 part by weight or more for aligning liquid crystal molecules, and approximately 10 parts by weight or less for avoiding a poor display, based on 100 parts by weight of the liquid crystal composition excluding the first component. A further preferred ratio is in the range of approximately 0.1 part by weight to approximately 2 parts by weight.

A preferred ratio of the second component is approximately 10% by weight or more for increasing the absolute value of the dielectric anisotropy, and approximately 90% by weight or less for decreasing the minimum temperature, based on the liquid crystal composition excluding the first component. A further preferred ratio is in the range of approximately 20% by weight to approximately 80% by weight. A particularly preferred ratio is in the range of approximately 30% by weight to approximately 70% by weight.

A preferred ratio of the third component is approximately 10% by weight or more for decreasing the viscosity or increasing the maximum temperature, and approximately 90% or less for increasing the absolute value of the dielectric anisotropy, based on the liquid crystal composition excluding the first component. A further preferred ratio is in the range of approximately 20% by weight to approximately 80% by weight. A particularly preferred ratio is in the range of approximately 30% by weight to approximately 70% by weight.

Fourth, the preferred embodiment of the component compounds will be explained. $R^1$, $R^2$, $R^3$, $R^4$, $R^5$ and $R^6$ are independently hydrogen, halogen, hydroxy, —$CH_2OH$, —$SF_5$, —$NO_2$, P-Sp- or alkyl having 1 to 30 carbons, the alkyl is straight-chain, branched-chain or cyclic, the alkyl may have an unsaturated bond, and in the alkyl, at least one of non-adjacent —$CH_2$— may be replaced by —O—, —S—, —CO—, —CO—O— or —O—CO—, and in the groups, at least one of hydrogen may be replaced by halogen, and at least one of $R^1$, $R^2$, $R^3$, $R^4$, $R^5$ and $R^6$ is P-Sp-. Two of arbitrary $R^4$ or $R^6$ when n is an integer from 2 to 12 may be identical or different. Preferred $R^1$, $R^2$, $R^3$, $R^4$, $R^5$ or $R^6$ is hydrogen, halogen, hydroxy, —$CH_2OH$, P-Sp- or alkyl having 1 to 10 carbons, the alkyl is straight-chain, branched-chain or cyclic, and the alkyl may have an unsaturated bond. Further preferred $R^1$, $R^2$, $R^3$, $R^4$, $R^5$ or $R^6$ is hydrogen, P-Sp- or alkyl having 1 to 10 carbons for increasing the stability to light or heat, the alkyl is straight-chain, branched-chain or cyclic, and the alkyl may have an unsaturated bond. Moreover, three to five of $R^1$, $R^2$, $R^3$, $R^4$, $R^5$ and $R^6$ is preferably P-Sp-. P is a polymerizable group. Preferred P is at least one group selected from the group of groups represented by formula (P-1) to formula (P-9). Further preferred P is acryloyloxy or methacryloyloxy for increasing photoreactivity. Sp is a single bond or alkylene having 1 to 20 carbons, and in the alkylene, at least one of hydrogen may be replaced by halogen or —CN, and in the groups, at least one of non-adjacent —$CH_2$— may be independently replaced by —O—, —S—, —NH—, —$NR^7$—, —$SiR^7R^8$—, —CO—, —COO—, —OCO—, —OCO—O—, —S—CO—, —CO—S—, —$NR^7$—CO—O—, —O—CO—$NR^7$—, —$NR^7$—CO—$NR^8$—, —CH═CH— or —C≡C—. Preferred Sp is well known to a person skilled in the art, and is straight-chain or branched-chain alkylene having 1 to 8 carbons. Further preferred Sp is a single bond.

$R^7$, $R^8$, $R^9$ and $R^{10}$ are independently hydrogen, halogen or alkyl having 1 to 12 carbons, the alkyl is straight-chain, branched-chain or cyclic, the alkyl may have an unsaturated bond, and in the alkyl, at least one of non-adjacent —$CH_2$— may be replaced by —O—, —S—, —CO—, —CO—O— or —O—CO—, and in the groups, at least one of hydrogen may be replaced by halogen. Preferred $R^7$, $R^8$, $R^9$ or $R^{18}$ is hydrogen, halogen or alkyl having 1 to 3 carbons for increasing the photoreactivity, the alkyl is straight-chain, branched-chain or cyclic, and the alkyl may have an unsaturated bond.

$R^{11}$, $R^{12}$, $R^{13}$ and $R^{14}$ are independently alkyl having 1 to 12 carbons, alkoxy having 1 to 12 carbons or alkenyl having 2 to 12 carbons, or alkenyl having 2 to 12 carbons in which at least one of hydrogen is replaced by fluorine. Preferred $R^{11}$ or $R^{12}$ is alkyl having 1 to 12 carbons for increasing the stability to ultraviolet light or heat, and alkoxy having 1 to 12 carbons for increasing the absolute value of the dielectric anisotropy. Preferred $R^{18}$ or $R^{14}$ is alkyl having 1 to 12 carbons for increasing the stability to ultraviolet light or heat, and alkenyl having 2 to 12 carbons for decreasing the minimum temperature.

In the first component, preferred alkyl is methyl, ethyl, propyl, isopropyl, butyl, isobutyl, t-butyl, pentyl, isopentyl, hexyl, isohexyl, heptyl, isoheptyl, octyl, isooctyl, cyclopropyl, cyclobutyl, 2-methylcyclopropyl, cyclopropylmethyl, cyclopentyl, cyclohexyl, trifluoromethyl, perfluoro-n-butyl, 2,2,2-trifluoroethyl, perfluorohexyl, vinyl, 1-propenyl, 2-propenyl, isopropenyl, 1-butenyl, 2-butenyl, 3-butenyl, 1-pentenyl, 2-pentenyl, 3-pentenyl, 4-pentenyl, 1-methyl-2-butenyl, 1-methyl-3-butenyl, 1,1-dimethyl-2-propenyl, 3-methyl-2-butenyl, 1-hexenyl, 2-hexenyl, 3-hexenyl, 4-hexenyl, 5-hexenyl, 2-methyl-1-pentenyl, 3-methyl-1-pentenyl, 4-methyl-1-pentenyl, 2-methyl-2-pentenyl, 3-methyl-2-pentenyl, 2-ethyl-1-butenyl, 3,3-dimethyl-1-butenyl, ethynyl, 1-propynyl, 2-propynyl, 1-butynyl, 2-butynyl, 3-butynyl, 1-pentynyl, 2-pentynyl, 3-pentynyl, 4-pentynyl, 4-methyl-1-pentenyl, 1-hexynyl, phenyl, naphthyl, anthryl, benzyl, methyloxy, ethyloxy, propyloxy, isopropyloxy, butyloxy, isobutyloxy, s-butyloxy, t-butyloxy, pentyloxy, isopentyloxy, hexyloxy, heptyloxy, cyclopropyloxy, cyclobutyloxy, 2-methylcyclopropyloxy, cyclopropylmethyloxy, cyclopentyloxy or cyclohexyloxy. Further preferred alkyl is methyl, ethyl, propyl, isopropyl, trifluoromethyl, 2,2,2-trifluoroethyl, vinyl, 1-propenyl, 2-propenyl, isopropenyl, ethynyl, 1-propynyl, 2-propynyl, methyloxy, ethyloxy, propyloxy or isopropyloxy for increasing the photoreactivity.

In the second component and the third component, preferred alkyl is methyl, ethyl, propyl, butyl, pentyl, hexyl, heptyl or octyl. Further preferred alkyl is ethyl, propyl, butyl, pentyl or heptyl for decreasing the viscosity.

Alkylene of the first component is straight-chain or branched-chain. Preferred straight-chain alkylene is ethylene, propylene, butylene, pentylene, hexylene, heptylene, octylene, nonylene, decylene, undecylene, dodecylene, ethyleneoxyethylene, methyleneoxybutylene, ethylenethioethylene, ethenylene, propenylene or butenylene. Preferred branched-chain alkylene is 1-methylethylene or 1-methylpropylene.

Preferred alkoxy is methoxy, ethoxy, propoxy, butoxy, pentyloxy, hexyloxy or heptyloxy. Further preferred alkoxy is methoxy or ethoxy for decreasing the viscosity.

Preferred alkenyl is vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl or 5-hexenyl. Further preferred alkenyl is vinyl, 1-propenyl, 3-butenyl or 3-pentenyl for decreasing the viscosity. A preferred configuration of —CH═CH— in the alkenyl depends on a position of a double bond. Trans is preferred in the alkenyl such as 1-propenyl, 1-butenyl, 1-pentenyl, 1-hexenyl, 3-pentenyl and 3-hexenyl for decreasing the viscosity, for instance. C is preferred in the alkenyl such as 2-butenyl, 2-pentenyl and 2-hexenyl. In the alkenyl, straight-chain alkenyl is preferred to branched-chain alkenyl.

Preferred examples of alkenyl in which at least one of hydrogen is replaced by fluorine include 2,2-difluorovinyl, 3,3-difluoro-2-propenyl, 4,4-difluoro-3-butenyl, 5,5-difluoro-4-pentenyl and 6,6-difluoro-5-hexenyl. Further preferred examples include 2,2-difluorovinyl and 4,4-difluoro-3-butenyl for decreasing the viscosity.

Ring A and ring C are independently 1,4-cyclohexylene, 1,4-phenylene, 1,4-phenylene in which at least one of hydrogen is replaced by fluorine or chlorine, or tetrahydropyran-2,5-diyl. Tetrahydropyran-2,5-diyl includes:

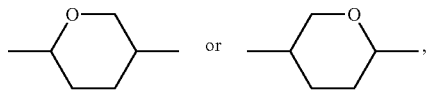

preferably,

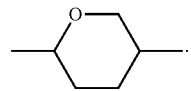

Tetrahydropyran-2,5-diyl is left-right asymmetric. However, the rings are defined to be allowed in a position not only in a defined direction but also in a reverse left-right direction as described above. The definition also applies to any other ring in which only one of left and right is defined in a left-right asymmetric ring.

Ring B is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl, and two of arbitrary ring A when p is 2 or 3 may be identical or different. Preferred ring A or ring C is 1,4-cyclohexylene for decreasing the viscosity. Preferred ring B is 2,3-difluoro-1,4-phenylene for decreasing the viscosity and increasing the absolute value of the dielectric anisotropy. Ring D and ring E are independently 1,4-cyclohexylene, 1,4-phenylene, 2-fluoro-1,4-phenylene or 3-fluoro-1,4-phenylene, and two of arbitrary ring D when s is 2 or 3 may be identical or different. Preferred ring D or ring E is 1,4-cyclohexylene for decreasing the viscosity, and 1,4-phenylene for increasing the optical anisotropy. With regard to a configuration of 1,4-cyclohexylene, trans is preferred to cis for increasing the maximum temperature. Then, "2-fluoro-1,4-phenylene" or the like is described by defining a left-side position on a ring as position 1, and "2-fluoro-1,4-phenylene" and "3-fluoro-1,4-phenylene" indicate that a position of fluorine is different.

$Z^1$, $Z^2$, $Z^3$, $Z^4$, $Z^5$ and $Z^6$ are independently a single bond, —O—, —S—, —CO—, —CO—O—, —O—CO—, —O—CO—O— or alkylene having 1 to 12 carbons. Two of arbitrary $Z^4$ or $Z^6$ when n is an integer from 2 to 12 may be identical or different. Preferred $Z^1$, $Z^2$, $Z^3$, $Z^4$, $Z^5$ or $Z^6$ is a single bond or —O— for increasing the photoreactivity. $Z^7$ is —O—, —S—, —CO—, —CO—O—, —O—CO—, —O—CO—O—, —OCH$_2$—, —CH$_2$O—, —SCH$_2$—, —CH$_2$S—, —CF$_2$O—, —OCF$_2$—, —CF$_2$S—, —SCF$_2$—, —(CR$^7$R$^8$)$_m$—, —(CR$^7$═CR$^8$)$_m$—, —C≡C—, —CR$^7$═CR$^8$—CO—O—, —O—CO—CR$^7$═CR$^8$—, —CO—NR$^7$—, —NR$^7$—CO—, —CO—S—, —S—CO—, —O—CO—CR$^7$R$^8$—O—, —O—CR$^7$═CR$^8$—CO—O—, —CR$^7$═CR$^8$—CO—, —CO—CR$^7$═CR$^8$—, —C(═CR$^7$R$^8$)—, —O—CO—CR$^7$R$^8$—CR$^9$—O— CR$^7$R$^8$—CR$^9$R$^{10}$—CO—O— or a single bond. Two of arbitrary $Z^7$ when n is an integer from 2 to 12 may be identical or different. Preferred $Z^7$ is —O—, —CO—, —CO—O—, —O—CO—, —O—CO—O—, —OCH$_2$—, —CH$_2$O—, —CF$_2$O—, —OCF$_2$—, —(CR$^7$R$^8$)$_m$— or a single bond. Further preferred $Z^7$ is —O—, —CH$_2$— or a single bond for increasing reactivity by exposure to ultraviolet light. $Z^8$, $Z^9$ and $Z^{10}$ are independently a single bond, ethylene, methyleneoxy or carbonyloxy, two of arbitrary $Z^8$ when p is 2 or 3 may be identical or different, and two of arbitrary $Z^{10}$ when s is 2 or 3 may be identical or different. Preferred $Z^8$ or $Z^9$ is a single bond for decreasing the viscosity, and methyleneoxy for increasing the absolute value of the dielectric anisotropy. Preferred $Z^{10}$ is a single bond for decreasing the viscosity.

$X^1$ and $X^2$ are independently hydrogen, —CH$_3$, —C$_2$H$_5$ or halogen. Preferred $X^1$ or $X^2$ is hydrogen for increasing the photoreactivity. $X^3$ is hydrogen, —CH$_3$, —C$_2$H$_5$, halogen or —CF$_3$. Preferred $X^3$ is hydrogen or —CH$_3$ for increasing the photoreactivity.

Then, m is 1, 2, 3 or 4. Preferred m is 1 or 2 for increasing the photoreactivity. Herein, n is an integer from 1 to 12. Preferred n is 1 or 2 for increasing the photoreactivity. Moreover, p is 1, 2 or 3, r is 0 or 1, and a sum of p and r is 3 or less. Preferred p is 1 for decreasing the minimum temperature. Preferred r is 0 for decreasing the viscosity. Furthermore, s is 1, 2 or 3. Preferred s is 1 for decreasing the viscosity, and 3 for increasing the maximum temperature.

Fifth, the specific examples of the component compounds will be shown. In the preferred compounds described below, $R^{15}$ and $R^{16}$ are independently hydrogen, hydroxy, acryloyloxy or methacryloyloxy. $R^{17}$ is straight-chain alkyl having 1 to 12 carbons or straight-chain alkoxy having 1 to 12 carbons. $R^{18}$ and $R^{19}$ are independently straight-chain alkyl having 1 to 12 carbons or straight-chain alkenyl having 2 to 12 carbons.

Preferred compound (1) includes compound (1-1-1) and compound (1-2-1). Further preferred compound (1) includes compound (1-1-1). Preferred compound (2) includes compound (2-1-1) to compound (2-19-1). Further preferred compound (2) includes compound (2-1-1), compound (2-2-1), compound (2-4-1), compound (2-6-1), compound (2-8-1), compound (2-11-1) and compound (2-13-1). Particularly preferred compound (2) includes compound (2-1-1), compound (2-4-1), compound (2-6-1), compound (2-8-1) and compound (2-13-1). Preferred compound (3) includes compound (3-1-1) to compound (3-13-1). Further preferred compound (3) includes compound (3-1-1), compound (3-3-1), compound (3-5-1), compound (3-7-1) and compound (3-9-1). Particularly preferred compound (3) includes compound (3-1-1), compound (3-5-1) and compound (3-7-1).

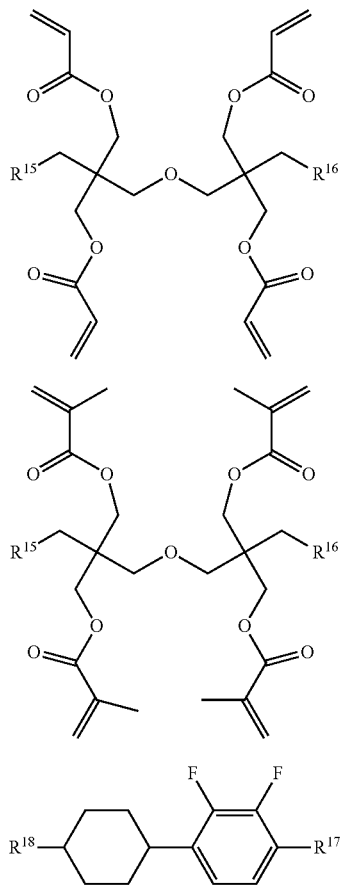

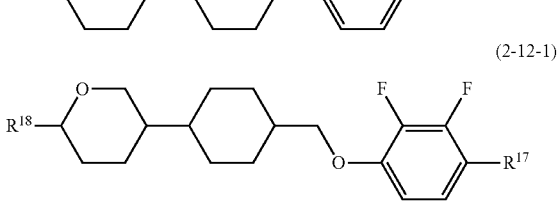

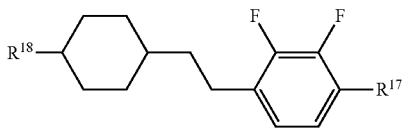

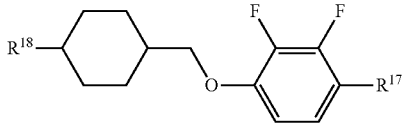

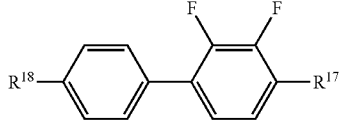

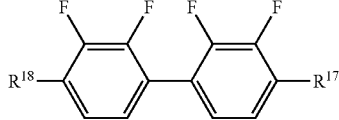

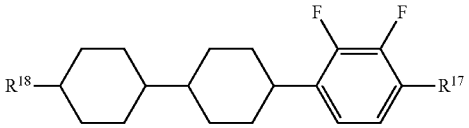

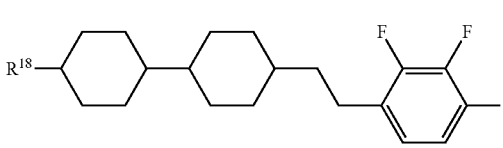

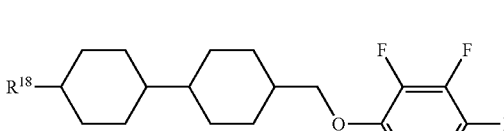

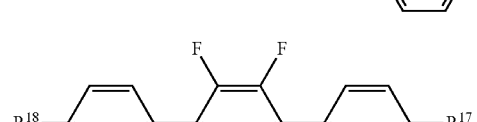

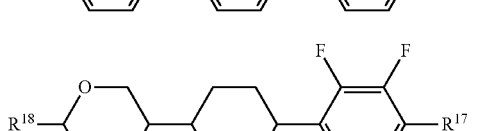

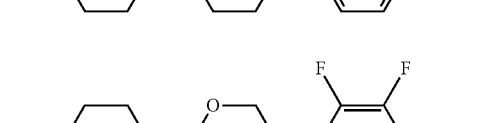

(2-13-1)
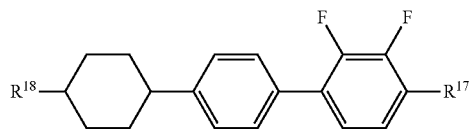

(2-14-1)
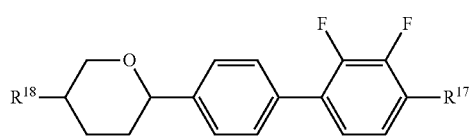

(2-15-1)
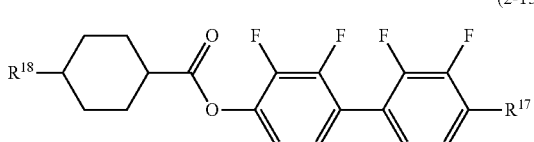

(2-16-1)
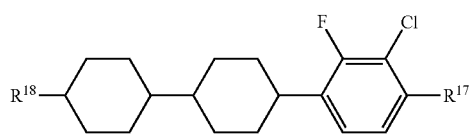

(2-17-1)
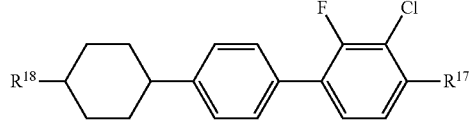

(2-18-1)
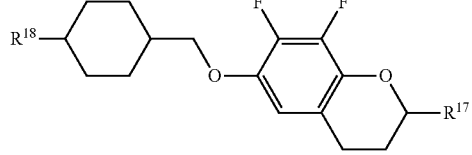

(2-19-1)
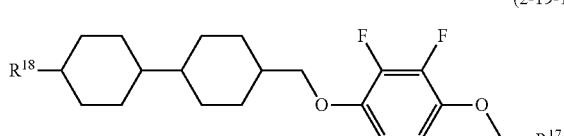

(3-1-1)
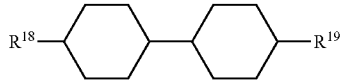

(3-2-1)
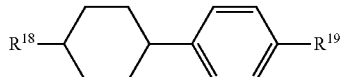

(3-3-1)
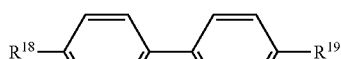

(3-4-1)
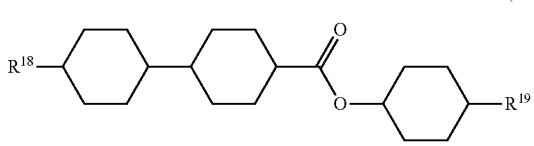

(3-5-1)

(3-6-1)

(3-7-1)
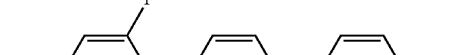

(3-8-1)
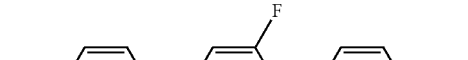

(3-9-1)
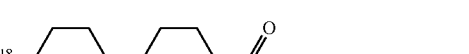

(3-10-1)
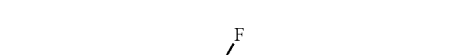

(3-11-1)
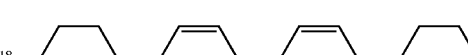

(3-12-1)
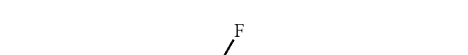

(3-13-1)

Sixth, the additive that may be mixed with the composition will be explained. Such an additive includes the optically active compound, the antioxidant, the ultraviolet light absorber, the dye, the antifoaming agent, the polymerization initiator and the polymerization inhibitor. The optically active compound is mixed with the composition for the purpose of inducing a helical structure in liquid crystals to give a twist angle. Examples of such a compound include compound (4-1) to compound (4-4). A preferred ratio of the optically active compound is approximately 5% by weight or less. A further preferred ratio is in the range of approximately 0.01% by weight to approximately 2% by weight.

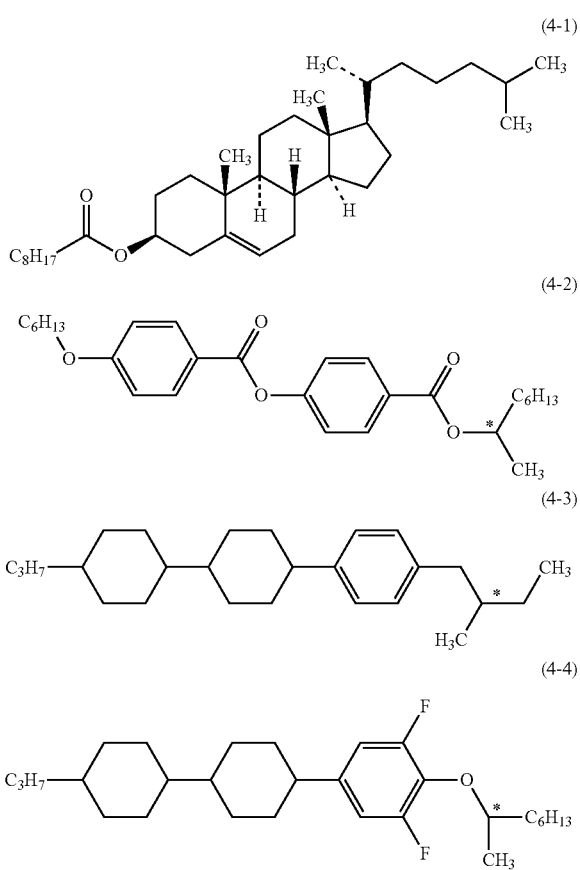

(4-1)
(4-2)
(4-3)
(4-4)

The antioxidant is mixed with the composition for the purpose of preventing a decrease in the specific resistance caused by heating in air, or maintaining a large voltage holding ratio at room temperature and also at a temperature close to the maximum temperature of the nematic phase even after the device has been used for a long period of time.

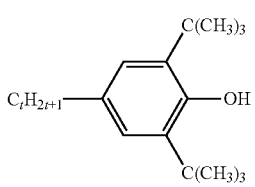

(5)

Preferred examples of the antioxidant include compound (5) where t is an integer from 1 to 9. In compound (5), preferred t is 1, 3, 5, 7 or 9. Further preferred t is 1 or 7. Compound (5) where t is 1 is effective in preventing a decrease in the specific resistance caused by heating in air because the compound (5) has a large volatility. Compound (5) where t is 7 is effective in maintaining a large voltage holding ratio at room temperature and also at a temperature close to the maximum temperature of the nematic phase even after the device has been used for a long period of time because the compound (5) has a small volatility. A preferred ratio of the antioxidant is approximately 50 ppm or more for achieving the effect thereof, and approximately 600 ppm or less for avoiding a decrease in the maximum temperature or avoiding an increase in the minimum temperature. A further preferred ratio is in the range of approximately 100 ppm to approximately 300 ppm.

Preferred examples of the ultraviolet light absorber include a benzophenone derivative, a benzoate derivative and a triazole derivative. A light stabilizer such as an amine having steric hindrance is also preferred. A preferred ratio of the ultraviolet light absorber or the stabilizer is approximately 50 ppm or more for achieving the effect thereof, and approximately 10,000 ppm or less for avoiding a decrease in the maximum temperature or avoiding an increase in the minimum temperature. A further preferred ratio is in the range of approximately 100 ppm to approximately 10,000 ppm.

A dichroic dye such as an azo dye or an anthraquinone dye is mixed with the composition to be adapted for a device having a guest host (GH) mode. A preferred ratio of the dye is in the range of approximately 0.01% by weight to approximately 10% by weight.

The antifoaming agent such as dimethyl silicone oil or methyl phenyl silicone oil is mixed with the composition for preventing foam formation. A preferred ratio of the antifoaming agent is approximately 1 ppm or more for achieving the effect thereof, and approximately 1,000 ppm or less for avoiding a poor display. A further preferred ratio is in the range of approximately 1 ppm to approximately 500 ppm.

The liquid crystal composition of the invention is suitable for use in the device having the polymer sustained alignment (PSA) mode because the composition contains the polymerizable compound. The composition may further contain a polymerizable compound other than compound (1). Preferred examples of the polymerizable compound include a compound having a polymerizable group, such as an acrylate, a methacrylate, a vinyl compound, a vinyloxy compound, a propenyl ether, an epoxy compound (oxirane, oxetane) and a vinyl ketone. Particularly preferred examples include an acrylate derivative or a methacrylate derivative. A preferred ratio of the polymerizable compound is approximately 0.05% by weight or more for achieving the effect thereof, and approximately 10% by weight or less for avoiding a poor display. A further preferred ratio is in the range of approximately 0.1% by weight to approximately 2% by weight. The polymerizable compound is preferably polymerized by irradiation with ultraviolet light or the like in the presence of a suitable initiator such as a photopolymerization initiator. Suitable conditions for polymerization, suitable types of the initiator and suitable amounts thereof are known to a person skilled in the art and are described in literatures. For example, Irgacure 651 (registered trademark; BASF), Irgacure 184 (registered trademark; BASF) or Darocure 1173 (registered trademark; BASF), each being a photoinitiator, is suitable for radical polymerization. A preferred ratio of the photopolymerization initiator is in the range of approximately 0.1% by weight to approximately 5% by weight of the polymerizable compound, and a further preferred ratio is in the range of approximately 1% by weight to approximately 3% by weight. A polymerized compound may be arranged through a process of arranging the liquid crystal composition containing the polymerizable compound between two substrates in the liquid crystal display device and polymerizing the polymerizable compound while applying a voltage between opposing electrode layers on the substrates, or a liquid crystal composition containing a preliminarily polymerized compound may be arranged between the two substrates in the liquid crystal display device.

Seventh, the methods for synthesizing the component compounds will be explained. The compounds can be prepared according to known methods. Examples of synthetic methods are shown. Compound (1-1-1) is commercially available from Shin-Nakamura Chemical Co., Ltd. Compound (2-1-1) is prepared by the method described in JP 2000-053602 A (2000). Compound (3-1-1) and compound (3-5-1) are prepared by the method described in JP S59-176221 A (1984). The antioxidant is commercially available. A compound represented by formula (5) where t is 1 is available from Sigma-Aldrich Corporation. Compound (5) where t is 7 and so forth are prepared according to the method described in U.S. Pat. No. 3,660,505 B.

Any compounds whose synthetic methods are not described above can be prepared according to the methods described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Koza in Japanese) (Maruzen Co., Ltd.). The composition is prepared according to publicly known methods using the thus obtained compounds. For example, the component compounds are mixed and dissolved in each other by heating.

Last, the application of the composition will be explained. Most of the compositions have a minimum temperature of approximately −10° C. or lower, a maximum temperature of approximately 70° C. or higher and an optical anisotropy in the range of approximately 0.07 to approximately 0.20. The device containing the composition has a large voltage holding ratio. The composition is suitable for use in the AM device. The composition is particularly suitable for use in a transmissive AM device. A composition having an optical anisotropy in the range of approximately 0.08 to approximately 0.25 may be prepared by controlling the ratio of the component compounds or by mixing with any other liquid crystal compound. The composition can be used as the composition having the nematic phase, and as the optically active composition by adding the optically active compound.

The composition can be used for the AM device. The composition can also be used for a PM device. The composition can be used for an AM device and a PM device both having a mode such as PC, TN, STN, ECB, OCB, IPS, VA or PSA. Use for the AM device having the PSA mode is particularly preferred. The devices may be of a reflective type, a transmissive type or a transflective type. Use for the transmissive device is preferred. The composition can also be used for an amorphous silicon-TFT device or a polycrystal silicon-TFT device. The composition can also be used for a nematic curvilinear aligned phase (NCAP) device prepared by microencapsulating the composition, and for a polymer dispersed (PD) device in which a three-dimensional network-polymer is formed in the composition.

The liquid crystal display device of the invention is characterized by comprising two substrates having an electrode layer on at least one of the substrates, and arranging between the two substrates the liquid crystal composition of the invention or a liquid crystal composition containing a compound formed by polymerization of the compound of the invention. For example, the liquid crystal display device comprises two glass substrates referred to as an array substrate and a color filter substrate, and a thin film transistor (TFT), pixels, a coloring layer and so forth are formed on each of the glass substrates. An aluminosilicate glass or aluminoborosilicate glass is used for each of the glass substrates, for example. For the electrode layer, Indium-Tin Oxide and Indium-Zinc Oxide are generally used.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

In order to evaluate characteristics of a composition and a compound to be contained in the composition, the composition and the compound were made a measurement object. When the measurement object was the composition, the measurement object was measured as a sample as is, and values obtained were described. When the measurement object was the compound, a sample for measurement was prepared by mixing the compound (15% by weight) into mother liquid crystals (85% by weight). Values of characteristics of the compound were calculated using values obtained by measurement, according to an extrapolation method: (extrapolated value)={(measured value of a sample for measurement)−0.85×(measured value of mother liquid crystals)}/0.15. When a smectic phase (or crystals) precipitated at the above ratio at 25° C., a ratio of the compound to the mother liquid crystals was changed step by step in the order of (10% by weight: 90% by weight), (5% by weight: 95% by weight) and (1% by weight: 99% by weight). Values of a maximum temperature, an optical anisotropy, viscosity and a dielectric anisotropy with regard to the compound were determined according to the extrapolation method.

Components of the mother liquid crystals and the ratio thereof were as described below.

$C_3H_7$—⬡—COO—⬡—$OC_2H_5$    17.2 wt %

$C_3H_7$—⬡—COO—⬡—$OC_4H_9$    27.6 wt %

$C_4H_9$—⬡—COO—⬡—$OC_2H_5$    20.7 wt %

$C_5H_{11}$—⬡—COO—⬡—$OCH_3$    20.7 wt %

$C_5H_{11}$—⬡—COO—⬡—$OC_2H_5$    13.8 wt %

Characteristics were measured according to the methods described below. Most of the methods are applied as described in Standard of Japan Electronics and Information Technology Industries Association, hereafter abbreviated as JEITA) discussed and established as Standard of JEITA (JEITA ED-2521B), or as modified thereon.

Maximum Temperature of a Nematic Phase (NI; ° C.):

A sample was placed on a hot plate in a melting point apparatus equipped with a polarizing microscope and was heated at a rate of 1° C. per minute. Temperature when a part of the sample began to change from a nematic phase to an isotropic liquid was measured. A higher limit of a temperature range of the nematic phase may be abbreviated as "maximum temperature."

Minimum Temperature of a Nematic Phase ($T_c$; ° C.):

A sample having a nematic phase was put in glass vials and kept in freezers at temperatures of 0° C., −10° C., −20° C., −30° C. and −40° C. for 10 days, and then liquid crystal phases were observed. For example, when the sample maintained the nematic phase at −20° C. and changed to crystals or a smectic phase at −30° C., $T_c$ was expressed as $T_c<-20°$ C. A lower limit of the temperature range of the nematic phase may be abbreviated as "minimum temperature."

Viscosity (Bulk Viscosity; q; Measured at 20° C.; mPa·s):

A cone-plate (E type) viscometer was used for measurement.

Optical Anisotropy (Refractive Index Anisotropy; Δn; Measured at 25° C.):

Measurement was carried out by means of an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of optical anisotropy was calculated from an equation: Δn=n∥−n⊥.

Dielectric Anisotropy (Δε; Measured at 25° C.):

A value of dielectric anisotropy was calculated from an equation: Δε=ε∥−ε⊥. A dielectric constant (ε∥ and ε⊥) was measured as described below.

(1) Measurement of dielectric constant (ε∥): An ethanol (20 mL) solution of octadecyl triethoxysilane (0.16 mL) was applied to a well-washed glass substrate. After rotating the glass substrate with a spinner, the glass substrate was heated at 150° C. for 1 hour. A sample was put in a VA device in which a distance (cell gap) between two glass substrates was 4 micrometers, and the device was sealed with an ultraviolet-curable adhesive. Sine waves (0.5 V, 1 kHz) were applied to the device, and after 2 seconds, a dielectric constant (ε⊥) in the major axis direction of liquid crystal molecules was measured.

(2) Measurement of dielectric constant (ε⊥): A polyimide solution was applied to a well-washed glass substrate. After calcining the glass substrate, rubbing treatment was applied to the alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant (ε⊥) in the minor axis direction of the liquid crystal molecules was measured.

Threshold Voltage (Vth; Measured at 25° C.; V):

An LCD-5100 luminance meter made by Otsuka Electronics Co., Ltd. was used for measurement. A light source was a halogen lamp. A sample was put in a normally black mode VA device in which a distance (cell gap) between two glass substrates was 4 micrometers and a rubbing direction was anti-parallel, and the device was sealed with an ultraviolet-curable adhesive. A voltage (60 Hz, rectangular waves) to be applied to the device was stepwise increased from 0 V to 20 V at an increment of 0.02 V. On the occasion, the device was irradiated with light from a direction perpendicular to the device, and the amount of light passing through the device was measured. A voltage-transmittance curve was prepared, in which the maximum amount of light corresponds to 100% transmittance and the minimum amount of light corresponds to 0% transmittance. A threshold voltage is voltage at 10% transmittance.

Voltage Holding Ratio (VHR-1; Measured at 25° C.; %):

A TN device used for measurement had a polyimide alignment film, and a distance (cell gap) between two glass substrates was 5 micrometers. A sample was put in the device, and then the device was sealed with an ultraviolet-curable adhesive. A pulse voltage (60 microseconds at 5 V) was applied to the TN device and the device was charged. A decaying voltage was measured for 16.7 milliseconds with a high-speed voltmeter, and area A between a voltage curve and a horizontal axis in a unit cycle was determined. Area B is an area without decay. A voltage holding ratio is a percentage of area A to area B.

Voltage Holding Ratio (VHR-2; Measured at 80° C.; %):

A TN device used for measurement had a polyimide alignment film, and a distance (cell gap) between two glass substrates was 5 micrometers. A sample was put in the device, and then the device was sealed with an ultraviolet-curable adhesive. A pulse voltage (60 microseconds at 5 V) was applied to the TN device and the device was charged. A decaying voltage was measured for 16.7 milliseconds with a high-speed voltmeter, and area A between a voltage curve and a horizontal axis in a unit cycle was determined. Area B is an area without decay. A voltage holding ratio is a percentage of area A to area B.

Voltage Holding Ratio (VHR-3; Measured at 25° C.; %):

Stability to ultraviolet light was evaluated by measuring a voltage holding ratio after a device was irradiated with ultraviolet light. A TN device used for measurement had a polyimide alignment film and a cell gap was 5 micrometers. A sample was injected into the device, and then the device was irradiated with light for 20 minutes. A light source was an ultra high-pressure mercury lamp USH-500D (made by Ushio, Inc.), and a distance between the device and the light source was 20 centimeters. In measuring VHR-3, a decaying voltage was measured for 16.7 milliseconds. A composition having a large VHR-3 has a large stability to ultraviolet light. A value of VHR-3 is preferably 90% or more, further preferably, 95% or more.

Voltage Holding Ratio (VHR-4; Measured at 25° C.; %):

A TN device into which a sample was injected was heated in a constant-temperature bath at 80° C. for 500 hours, and then stability to heat was evaluated by measuring a voltage holding ratio. In measuring VHR-4, a decaying voltage was measured for 16.7 milliseconds. A composition having a large VHR-4 has a large stability to heat.

Response Time (t; Measured at 25° C.; Ms):

An LCD-5100 luminance meter made by Otsuka Electronics Co., Ltd. was used for measurement. A light source was a halogen lamp. A low-pass filter was set at 5 kHz. A sample was put in a normally black mode PVA device in which a distance (cell gap) between two glass substrates was 3.2 micrometers and a rubbing direction was anti-parallel, and the device was sealed with an ultraviolet-curable adhesive. The device was irradiated with ultraviolet light of 25 mW/cm² (EXECURE4000-D lamp made by HOYA CANDEO OPTRONICS CORPORATION) for 400 seconds while applying a voltage of 15 V. Rectangular waves (60 Hz, 10 V, 0.5 second) were applied to the device. On the occasion, the device was irradiated with light from a direction perpendicular to the device, and the amount of light passing through the device was measured. The maximum amount of light corresponds to 100% transmittance, and the minimum amount of light corresponds to 0% transmittance.

A response time is a period of time required for a change from 0% transmittance to 90% transmittance (rise time; millisecond).

Specific Resistance (ρ; Measured at 25° C.; Ω·Om):

Into a vessel equipped with an electrode, 1.0 milliliter of a sample was injected. A DC voltage (10 V) was applied to the vessel, and a DC current after 10 seconds was measured. A specific resistance was calculated from the following equation: (specific resistance)={(voltage)×(electric capacity of a vessel)}/{(DC current)×(dielectric constant of vacuum)}.

Gas Chromatographic Analysis:

GC-14B Gas Chromatograph made by Shimadzu Corporation was used for measurement. A carrier gas was helium (2 mL per minute). A sample injector and a detector (FID) were set to 280° C. and 300° C., respectively. A capillary column DB-1 (length 30 m, bore 0.32 mm, film thickness 0.25 μm; dimethylpolysiloxane as a stationary phase, non-polar) made by Agilent Technologies, Inc. was used for separation of component compounds. After the column was kept at 200° C. for 2 minutes, the column was heated to 280° C. at a rate of 5° C. per minute. A sample was prepared in an acetone solution (0.1% by weight), and then 1 microliter of the solution was injected into the sample injector. A recorder was C-R5A Chromatopac made by Shimadzu Corporation or the equivalent thereof. The resulting gas chromatogram showed a retention time of a peak and a peak area corresponding to each of the component compounds.

As a solvent for diluting the sample, chloroform, hexane and so forth may also be used. The following capillary columns may also be used for separating component compounds: HP-1 (length 30 m, bore 0.32 mm, film thickness 0.25 μm) made by Agilent Technologies, Inc., Rtx-1 (length 30 m, bore 0.32 mm, film thickness 0.25 μm) made by Restek Corporation and BP-1 (length 30 m, bore 0.32 mm, film thickness 0.25 μm) made by SGE International Pty. Ltd. A capillary column CBP1-M50-025 (length 50 m, bore 0.25 mm, film thickness 0.25 μm) made by Shimadzu Corporation may also be used for the purpose of avoiding an overlap of peaks of the compounds.

A ratio of liquid crystal compounds included in the composition may be calculated by the method as described below. The liquid crystal compounds can be detected by means of a gas chromatograph. A ratio of peak areas in a gas chromatogram corresponds to a ratio (in the number of moles) of the liquid crystal compounds. When the capillary columns described above were used, a correction coefficient of each of the liquid crystal compounds may be regarded as 1 (one). Accordingly, a ratio (% by weight) of the liquid crystal compounds was calculated from the ratio of the peak areas.

The invention will be explained in detail by way of Examples. The invention is not limited by the Examples described below. The compounds in Comparative Examples and Examples were described using symbols according to definitions in Table 3 below. In Table 3, a configuration of 1,4-cyclohexylene is trans. A parenthesized number next to a symbolized compound corresponds to the number of the compound. A symbol (-) means any other liquid crystal compound. A ratio (percentage) of the liquid crystal compounds is expressed in terms of weight percent (% by weight) based on the weight of the liquid crystal composition excluding the first composition. The liquid crystal composition further includes an impurity in addition thereto. Last, values of characteristics of the composition were summarized.

TABLE 3

Method for Description of Compounds using Symbols
$R-(A_1)-Z_1-\ldots-Z_n-(A_n)-R'$

| 1) Left-terminal Group R— | Symbol |
|---|---|
| $C_nH_{2n+1}-$ | n- |
| $C_nH_{2n+1}O-$ | nO— |
| $C_mH_{2m+1}OC_nH_{2n}-$ | mOn— |
| $CH_2=CH-$ | V— |
| $C_nH_{2n+1}-CH=CH-$ | nV— |
| $CH_2=CH-C_nH_{2n}-$ | Vn— |
| $C_mH_{2m+1}-CH=CH-C_nH_{2n}-$ | mVn— |
| $CF_2=CH-$ | VFF— |
| $CF_2=CH-C_nH_{2n}-$ | VFFn— |
| $CH_2=CHCOO-$ | AC— |
| $CH_2=C(CH_3)COO-$ | MAC— |

| 2) Right-terminal Group —R' | Symbol |
|---|---|
| $-C_nH_{2n+1}$ | -n |
| $-OC_nH_{2n+1}$ | —On |
| $-CH=CH_2$ | —V |
| $-CH=CH-C_nH_{2n+1}$ | —Vn |
| $-C_nH_{2n}-CH=CH_2$ | —nV |
| $-CH=CF_2$ | —VFF |
| $-COOCH_3$ | —EMe |
| $-OCOCH=CH_2$ | —AC |
| $-OCOC(CH_3)=CH_2$ | —MAC |

| 3) Bonding Group —$Z_n$— | Symbol |
|---|---|
| $-C_2H_4-$ | 2 |
| $-COO-$ | E |
| $-CH=CH-$ | V |
| $-C\equiv C-$ | T |
| $-CF_2O-$ | X |
| $-CH_2O-$ | 1O |
| $-SiH_2-$ | Si |

| 4) Ring Structure —$A_n$— | Symbol |
|---|---|
|  | H |
| 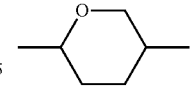 | Dh |
|  | dh |
| 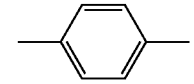 | B |
| 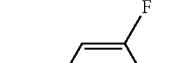 | B(F) |
| 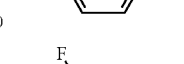 | B(2F) |

TABLE 3-continued

Method for Description of Compounds using Symbols
R—(A₁)—Z₁— . . . —Zₙ—(Aₙ)—R'

| Structure | Symbol |
|---|---|
| (difluorobenzene) | B(2F,5F) |
| (difluorobenzene) | B(2F,3F) |
| (methyl difluorobenzene) | B(2F,3F,6Me) |
| (fluoro chloro benzene) | B(2F,3CL) |
| (naphthalene) | Np |
| (trifluoronaphthalene) | Np(3F,4F,5F) |
| (difluorochromane) | Cro(7F,8F) |

5) Examples of Description

Example 1 3-HB(2F,3F)-O2

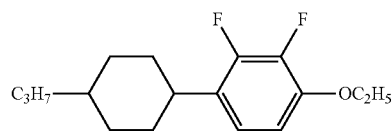

Example 2 3-HDhB(2F,3F)-O2

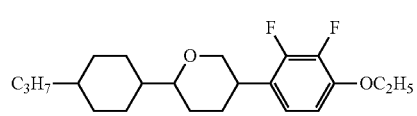

Comparative Example 1

The composition is a liquid crystal composition without containing a first component of the invention. Components and characteristics of the composition are as described below.

| Compound | Code | % |
|---|---|---|
| 3-BB(2F,3F)-O2 | (2-4-1) | 8% |
| 5-BB(2F,3F)-O2 | (2-4-1) | 10% |
| 2-HH1OB(2F,3F)-O2 | (2-8-1) | 5% |
| 3-HH1OB(2F,3F)-O2 | (2-8-1) | 10% |
| 3-DhHB(2F,3F)-O2 | (2-10-1) | 5% |
| 3-HDhB(2F,3F)-O2 | (2-11-1) | 6% |
| 5-DhH1OB(2F,3F)-O2 | (2-12-1) | 3% |
| 3-dhBB(2F,3F)-O2 | (2-14-1) | 6% |
| 3-HEB(2F,3F)B(2F,3F)-O4 | (2-15-1) | 4% |
| 2-HH-3 | (3-1-1) | 16% |
| 3-HH-4 | (3-1-1) | 5% |
| 1-BB-3 | (3-3-1) | 5% |
| 3-HHB-1 | (3-5-1) | 3% |
| 3-HHB-3 | (3-5-1) | 3% |
| V-HHB-1 | (3-5-1) | 3% |
| 5-B(F)BB-2 | (3-7-1) | 4% |
| 5-B(F)BB-2 | (3-7-1) | 4% |

NI = 85.6° C.;
Tc < −20° C.;
Δn = 0.120;
Δε = −3.9;
Vth = 2.07 V;
τ = 8.0 ms;
VHR-1 = 99.2%;
VHR-2 = 98.1%.

Example 1

| Compound | Code | % |
|---|---|---|
| 3-BB(2F,3F)-O2 | (2-4-1) | 8% |
| 5-BB(2F,3F)-O2 | (2-4-1) | 10% |
| 2-HH1OB(2F,3F)-O2 | (2-8-1) | 5% |
| 3-HH1OB(2F,3F)-O2 | (2-8-1) | 10% |
| 3-DhHB(2F,3F)-O2 | (2-10-1) | 5% |
| 3-HDhB(2F,3F)-O2 | (2-11-1) | 6% |
| 5-DhH1OB(2F,3F)-O2 | (2-12-1) | 3% |
| 3-dhBB(2F,3F)-O2 | (2-14-1) | 6% |
| 3-HEB(2F,3F)B(2F,3F)-O4 | (2-15-1) | 4% |
| 2-HH-3 | (3-1-1) | 16% |
| 3-HH-4 | (3-1-1) | 5% |
| 1-BB-3 | (3-3-1) | 5% |
| 3-HHB-1 | (3-5-1) | 3% |
| 3-HHB-3 | (3-5-1) | 3% |
| V-HHB-1 | (3-5-1) | 3% |
| 5-B(F)BB-2 | (3-7-1) | 4% |
| 5-B(F)BB-2 | (3-7-1) | 4% |

Into 100 parts by weight of the composition, 0.40 part by weight of compound (1-1-1-1) described below was added.

(1-1-1-1)

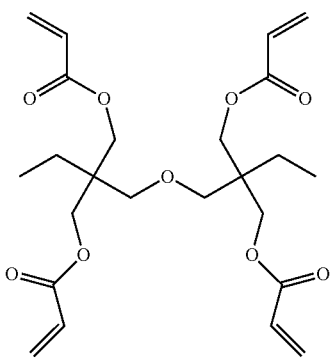

NI=85.5° C.; Tc<−20° C.; Δn=0.120; Δε=−3.9; Vth=2.06 V; τ=5.9 ms; VHR-1=99.2%; VHR-2=98.1%.

Example 2

| | | |
|---|---|---|
| 3-H2B(2F,3F)-O2 | (2-2-1) | 19% |
| 5-H2B(2F,3F)-O2 | (2-2-1) | 15% |
| 5-HH2B(2F,3F)-O2 | (2-7-1) | 5% |
| 3-HBB(2F,3F)-O2 | (2-13-1) | 10% |
| 5-HBB(2F,3F)-O2 | (2-13-1) | 4% |
| 3-HHB(2F,3CL)-O2 | (2-16-1) | 3% |
| V-HBB(2F,3CL)-O2 | (2-17-1) | 3% |
| 2-HH-3 | (3-1-1) | 25% |
| 3-HHEH-3 | (3-4-1) | 3% |
| 3-HHB-O1 | (3-5) | 4% |
| 3-HBB-2 | (3-6-1) | 3% |
| 3-HB(F) HH-5 | (3-10-1) | 3% |
| 5-HBBH-3 | (3-11-1) | 3% |

Into 100 parts by weight of the composition, 0.3 part by weight of compound (1-1-1-1) described below was added.

(1-1-1-1)

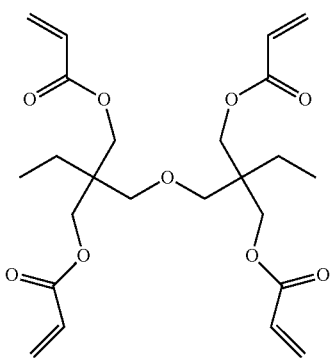

NI=81.0° C.; Tc<−20° C.; Δn=0.090; Δε=−2.8; Vth=2.38 V; τ=5.3 ms; VHR-1=99.2%; VHR-2=97.6%.

Example 3

| | | |
|---|---|---|
| 3-H2B(2F,3F)-O2 | (2-2-1) | 20% |
| 5-H2B(2F,3F)-O2 | (2-2-1) | 15% |
| 2-BB(2F,3F)B-3 | (2-9-1) | 7% |
| 3-DhHB(2F,3F)-O2 | (2-10-1) | 5% |
| 3-HBB(2F,3F)-O2 | (2-13-1) | 10% |
| 4-HBB(2F,3F)-O2 | (2-13-1) | 5% |
| 3-H1OCro(7F,8F)-5 | (2-18-1) | 3% |
| 3-HH1OCro(7F,8F)-5 | (2-19-1) | 3% |
| 2-HH-3 | (3-1-1) | 15% |
| 3-HH-4 | (3-1-1) | 5% |
| 3-HHB-O1 | (3-5) | 3% |
| 3-HHEBH-3 | (3-9-1) | 3% |
| 3-HB(F)BH-3 | (3-12-1) | 3% |
| 5-HBB(F)B-2 | (3-13-1) | 3% |

Into 100 parts by weight of the composition, 0.3 part by weight of compound (1-1-1-1) described below was added.

(1-1-1-1)

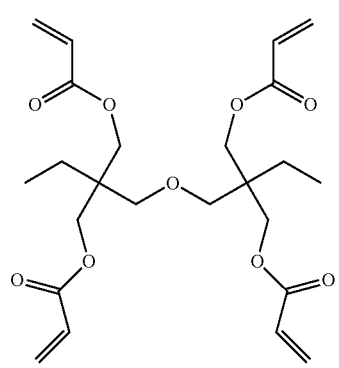

NI=79.8° C.; Tc<−20° C.; Δn=0.105; Δε=−3.8; Vth=2.11 V; τ=5.5 ms; VHR-1=99.3%; VHR-2=97.9%.

Example 4

| | | |
|---|---|---|
| 3-H2B(2F,3F)-O2 | (2-2-1) | 20% |
| 5-H2B(2F,3F)-O2 | (2-2-1) | 12% |
| 3-HHB(2F,3F)-O2 | (2-6-1) | 8% |
| 3-HHB(2F,3F)-1 | (2-6-1) | 5% |
| 3-HDhB(2F,3F)-O2 | (2-11-1) | 5% |
| 3-HBB(2F,3F)-O2 | (2-13-1) | 10% |
| 4-HBB(2F,3F)-O2 | (2-13-1) | 6% |
| 5-HBB(2F,3F)-O2 | (2-13-1) | 3% |
| 2-HH-3 | (3-1-1) | 10% |
| 3-HH-4 | (3-1-1) | 10% |
| 1V-HH-3 | (3-1-1) | 8% |
| 3-HHB-1 | (3-5-1) | 3% |

Into 100 parts by weight of the composition, 0.4 part by weight of compound (1-1-1-1) described below was added.

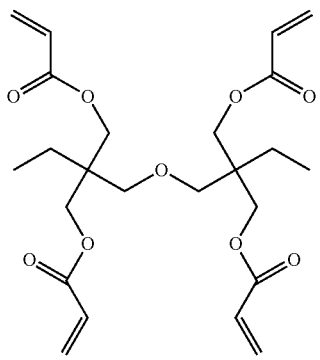

(1-1-1-1)

NI=77.2° C.; Tc<−20° C.; Δn=0.090; Δε=−3.6; Vth=2.09 V; τ=5.2 ms; VHR-1=99.1%; VHR-2=98.2%.

Example 5

| | | |
|---|---|---|
| 3-BB(2F,3F)-O2 | (2-4-1) | 9% |
| 5-BB(2F,3F)-O2 | (2-4-1) | 6% |
| 2-HH1OB(2F,3F)-O2 | (2-8-1) | 13% |
| 3-HH1OB(2F,3F)-O2 | (2-8-1) | 21% |
| 2-HH-3 | (3-1-1) | 20% |
| 3-HH-4 | (3-1-1) | 8% |
| 3-HB-O2 | (3-2) | 5% |
| 1-BB-3 | (3-3-1) | 7% |
| 3-HHB-1 | (3-5-1) | 3% |
| 3-HHB-O1 | (3-5) | 4% |
| 5-B(F)BB-2 | (3-7-1) | 4% |

Into 100 parts by weight of the composition, 0.3 part by weight of compound (1-1-1-1) described below was added.

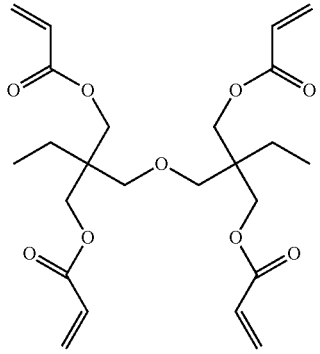

(1-1-1-1)

NI=75.8° C.; Tc<−20° C.; Δn=0.100; Δε=−3.3; Vth=2.22 V; τ=4.2 ms; VHR-1=99.0%; VHR-2=97.9%.

Example 6

| | | |
|---|---|---|
| 3-HB(2F,3F)-O2 | (2-1-1) | 12% |
| V-HB(2F,3F)-O2 | (2-1-1) | 11% |
| V-HB(2F,3F)-O4 | (2-1-1) | 8% |
| 1V2-HB(2F,3F)-O2 | (2-1-1) | 4% |
| 3-HBB(2F,3F)-O2 | (2-13-1) | 10% |
| 4-HBB(2F,3F)-O2 | (2-13-1) | 6% |
| 5-HBB(2F,3F)-O2 | (2-13-1) | 10% |

-continued

| | | |
|---|---|---|
| 3-HH1OCro(7F,8F)-5 | (2-19-1) | 5% |
| V-HH-3 | (3-1-1) | 13% |
| VFF-HH-3 | (3-1) | 5% |
| 3-HHB-1 | (3-5-1) | 3% |
| 3-HHB-O1 | (3-5) | 3% |
| 3-HHB-3 | (3-5-1) | 3% |
| 5-HBB(F)B-2 | (3-13-1) | 4% |
| 1O1-HBBH-5 | (—) | 3% |

Into 100 parts by weight of the composition, 0.2 part by weight of compound (1-1-1-1) described below,

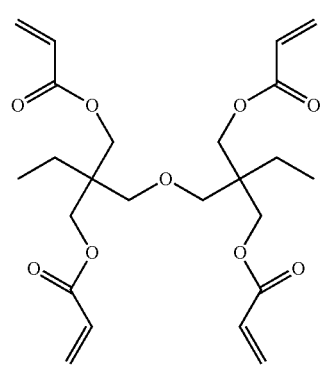

(1-1-1-1)

and 0.2 part by weight of compound (1-2-1-1) described below were added.

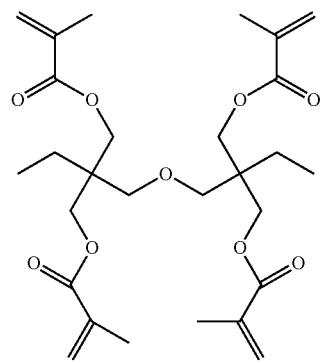

(1-2-1-1)

NI=84.7° C.; Tc<−20° C.; Δn=0.108; Δε=−3.7; Vth=1.94 V; τ=6.4 ms; VHR-1=99.1%; VHR-2=97.9%.

Example 7

| | | |
|---|---|---|
| 3-H1OB(2F,3F)-O2 | (2-3-1) | 6% |
| 3-BB(2F,3F)-O2 | (2-4-1) | 6% |
| 5-BB(2F,3F)-O2 | (2-4-1) | 5% |
| 2O-B(2F,3F)B(2F,3F)-O6 | (2-5) | 3% |
| 2-HH1OB(2F,3F)-O2 | (2-8-1) | 10% |
| 3-HH1OB(2F,3F)-O2 | (2-8-1) | 15% |
| 2-HH-3 | (3-1-1) | 20% |
| 3-HH-4 | (3-1-1) | 9% |
| 3-HH-O1 | (3-1) | 5% |
| 3-HB-O2 | (3-2) | 3% |
| V2-BB-1 | (3-3-1) | 5% |
| 3-HHB-1 | (3-5-1) | 3% |
| 3-HHB-O1 | (3-5) | 3% |

| | | |
|---|---|---|
| 1-BB(F)B-2V | (3-8-1) | 3% |
| 3-HHEBH-4 | (3-9-1) | 4% |

Into 100 parts by weight of the composition, 0.15 part by weight of compound (1-1-1-1) described below,

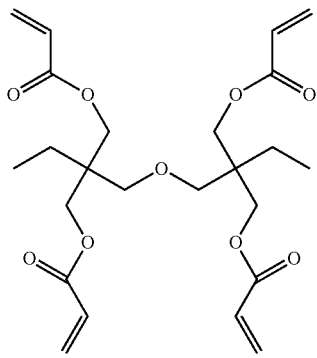
(1-1-1-1)

and 0.15 part by weight of compound (1-2-1-1) described below were added.

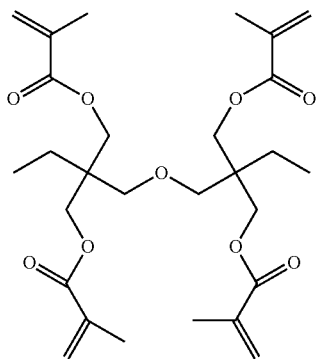
(1-2-1-1)

NI=74.6° C.; Tc<−20° C.; Δn=0.090; Δε=−3.3; Vth=2.20 V; τ=4.0 ms; VHR-1=99.3%; VHR-2=98.0%.

Example 8

| | | |
|---|---|---|
| 3-H1OB(2F,3F)-O2 | (2-3-1) | 6% |
| 3-BB(2F,3F)-O2 | (2-4-1) | 6% |
| 5-BB(2F,3F)-O2 | (2-4-1) | 5% |
| 2O-B(2F,3F)B(2F,3F)-O6 | (2-5) | 3% |
| 2-HH1OB(2F,3F)-O2 | (2-8-1) | 10% |
| 3-HH1OB(2F,3F)-O2 | (2-8-1) | 15% |
| 2-HH-3 | (3-1-1) | 20% |
| 3-HH-4 | (3-1-1) | 8% |
| 3-HH-O1 | (3-1) | 5% |
| 3-HB-O2 | (3-2) | 3% |
| V2-BB-1 | (3-3-1) | 5% |
| 3-HHB-1 | (3-5-1) | 3% |
| 3-HHB-O1 | (3-5) | 4% |
| 1-BB(F)B-2V | (3-8-1) | 3% |
| 3-HHEBH-4 | (3-9-1) | 4% |

Into 100 parts by weight of the composition, 0.3 part by weight of compound (1-2-1-1) described below was added.

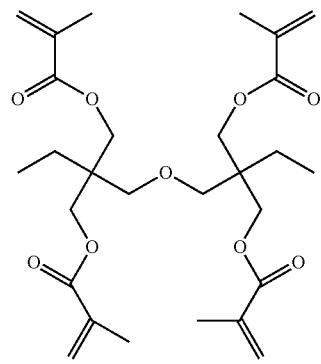
(1-2-1-1)

NI=75.8° C.; Tc<−20° C.; Δn=0.091; Δε=−3.3; Vth=2.21 V; τ=4.1 ms; VHR-1=99.3%; VHR-2=97.9%.

The compositions according to Examples 1 to 8 have a shorter response time in comparison with the composition according to Comparative Example 1.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

INDUSTRIAL APPLICABILITY

The invention concerns a liquid crystal composition satisfying at least one of characteristics such as a high maximum temperature of a nematic phase, a low minimum temperature of the nematic phase, a small viscosity, a suitable optical anisotropy, a large negative dielectric anisotropy, a large specific resistance, a high stability to ultraviolet light and a high stability to heat, or a liquid crystal composition having a suitable balance regarding at least two of the characteristics is provided. A liquid crystal display device containing such a liquid crystal composition is applied to constitute an AM device having a short response time, a large voltage holding ratio, a large contrast ratio, a long service life and so forth, and thus can be used for a liquid crystal projector, a liquid crystal television and so forth.

The invention claimed is:

1. A liquid crystal composition having a dielectric anisotropy (25° C.) at a frequency of 1 kHz is −2 or less and containing at least one compound selected from the group of compounds represented by formula (1) as a first component further containing at least one compound selected from the group of compounds represented by formula (2) as a second component:

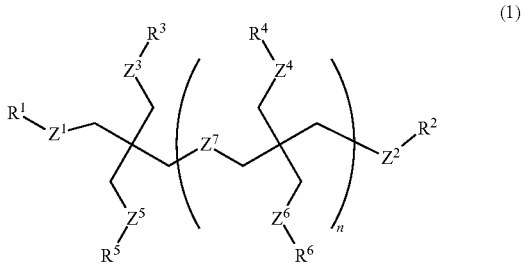
(1)

-continued

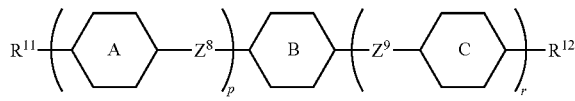 (2)

wherein $R^1$, $R^2$, $R^3$, $R^4$, $R^5$ and $R^6$ are independently hydrogen, halogen, hydroxy, —CH$_2$OH, —SF$_5$, —NO$_2$, P—Sp- or alkyl having 1 to 30 carbons, the alkyl is straight-chain, branched-chain or cyclic, the alkyl may have an unsaturated bond, and in the alkyl, at least one of non-adjacent —CH$_2$— may be replaced by —O—, —S—, —CO—, —CO—O— or —O—CO—, and in the groups, at least one of hydrogen may be replaced by halogen;

P is a polymerizable group;

Sp is a single bond or alkylene having 1 to 20 carbons, and in the alkylene, at least one of hydrogen may be replaced by halogen or —C≡N, and in the groups, at least one of non-adjacent —CH$_2$— may be independently replaced by —O—, —S—, —NH—, —NR$^7$—, —SiR$^7$R$^8$—, —CO—, —COO—, —OCO—, —OCO—O—, —S—CO—, —CO—S—, —NR$^7$—CO—O—, —O—CO—NR$^7$—, —NR$^7$—CO—NR$^8$—, —CH═CH— or —C≡C—;

at least one of $R^1$, $R^2$, $R^3$, $R^4$, $R^5$ and $R^6$ is P—Sp-;

$Z^1$, $Z^2$, $Z^3$, $Z^4$, $Z^5$ and $Z^6$ are independently a single bond, —O—, —S—, —CO—, —CO—O—, —O—CO—, —O—CO—O— or alkylene having 1 to 12 carbons;

$Z^7$ is independently —O—, —S—, —CO—, —CO—O—, —O—CO—, —O—CO—O—, —OCH$_2$—, —CH$_2$O—, —SCH$_2$—, —CH$_2$S—, —CF$_2$O—, —OCF$_2$—, —CF$_2$S—, —SCF$_2$—, —(CR$^7$R$^8$)$_m$—, —(CR$^7$═CR$^8$)$_m$—, —C≡C—, —CR$^7$═CR$^8$—CO—O—, —O—CO—CR$^7$═CR$^8$—, —CO—NR$^7$—, —NR$^7$—CO—, —CO—S—, —S—CO—, —O—CO—CR$^7$═CR$^8$—O—, —O—CR$^7$═CR$^8$—CO—O—, —CR$^7$═CR$^8$—CO—, —CO—CR$^7$═CR$^8$—, —C(═CR$^7$R$^8$)—, —O—CO—CR$^7$R$^8$—CR$^9$R$^{10}$—O—, —O—CR$^7$R$^8$—CR$^9$R$^{10}$—CO—O— or a single bond;

$R^7$, $R^8$, $R^9$ and $R^{10}$ are independently hydrogen, halogen or alkyl having 1 to 12 carbons, the alkyl is straight-chain, branched-chain or cyclic, the alkyl may have an unsaturated bond, and in the alkyl, at least one of non-adjacent —CH$_2$— may be replaced by —O—, —S—, —CO—, —CO—O—, or —O—CO—, and in the groups, at least one of hydrogen may be replaced by halogen; m is 1, 2, 3 or 4; and n is an integer from 1 to 12;

$R^{11}$ and $R^{12}$ are independently alkyl having 1 to 12 carbons, alkoxy having 1 to 12 carbons or alkenyl having 2 to 12 carbons, or alkenyl having 2 to 12 carbons in which at least one of hydrogen is replaced by fluorine;

ring A and ring C are independently 1,4-cyclohexylene, 1,4-phenylene, 1,4-phenylene in which at least one of hydrogen is replaced by fluorine or chlorine, or tetrahydropyran-2,5-diyl; ring B is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl;

$Z^8$ and $Z^9$ are independently a single bond, ethylene, methyleneoxy or carbonyloxy; p is 1, 2 or 3; r is 0 or 1; and a sum of p and r is 3 or less;

wherein when the composition is used in an active matrix (AM) device, it has a response time ranging from 4.0 to 5.9 ms.

2. The liquid crystal composition according to claim 1, wherein, in formula (1), $R^1$, $R^2$, $R^3$, $R^4$, $R^5$ and $R^6$ are independently hydrogen, hydroxy, alkyl having 1 to 12 carbons, alkoxy having 1 to 12 carbons, alkenyl having 2 to 12 carbons, alkenyl having 2 to 12 carbons in which at least one of hydrogen is replaced by fluorine, or a group selected from the group of groups represented by formula (P-1) to formula (P-9);

and at least one of $R^1$, $R^2$, $R^3$, $R^4$, $R^5$ and $R^6$ is a group selected from the group of groups represented by formula (P-1) to formula (P-9):

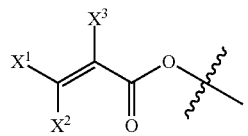 (P-1)

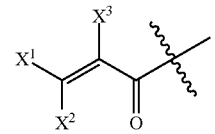 (P-2)

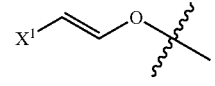 (P-3)

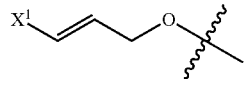 (P-4)

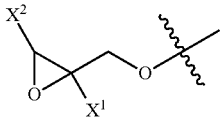 (P-5)

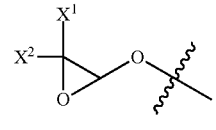 (P-6)

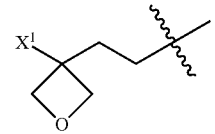 (P-7)

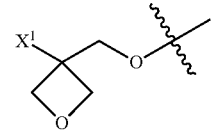 (P-8)

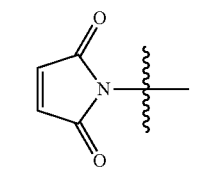 (P-9)

wherein $X^1$ and $X^2$ are independently hydrogen, —CH$_3$, —C$_2$H$_5$ or halogen; and $X^3$ is hydrogen, —CH$_3$, —C$_2$H$_5$, halogen or —CF$_3$.

3. The liquid crystal composition according to claim 1, wherein the first component is at least one compound selected from the group of compounds represented by formula (1-1) to formula (1-2):

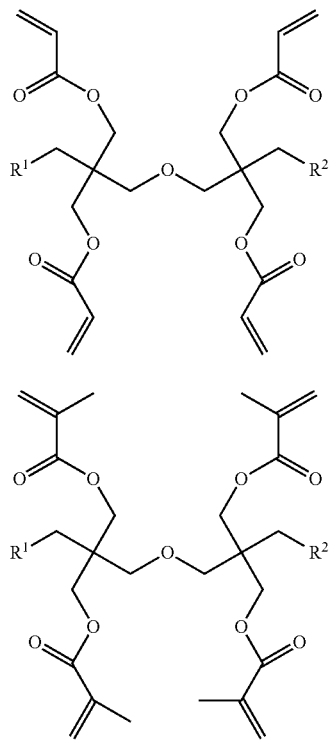

(1-1)

(1-2)

wherein $R^1$ and $R^2$ are independently hydrogen, halogen, hydroxy, —CH$_2$OH, —SF$_5$, —NO$_2$, P— or alkyl having 1 to 12 carbons, the alkyl is straight-chain, branched-chain or cyclic, the alkyl may have an unsaturated bond, and in the alkyl, at least one of non-adjacent —CH$_2$— may be replaced by —O—, —S—, —CO—, —CO—O— or —O—CO—, and in the groups, at least one of hydrogen may be replaced by halogen; and P is acryloyloxy or methacryloyloxy.

4. The liquid crystal composition according to claim 1, wherein a ratio of the first component is in the range of 0.05 part by weight to 10 parts by weight based on 100 parts by weight of a liquid crystal composition excluding the first component.

5. The liquid crystal composition according to claim 1, wherein the second component is at least one compound selected from the group of compounds represented by formula (2-1) to formula (2-19):

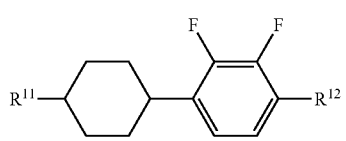

(2-1)

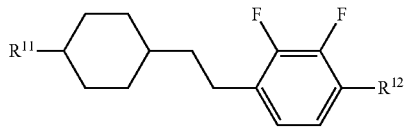

(2-2)

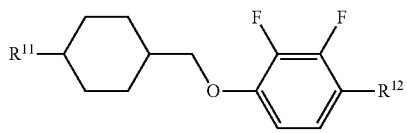

(2-3)

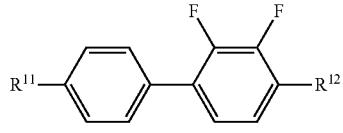

(2-4)

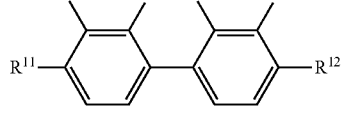

(2-5)

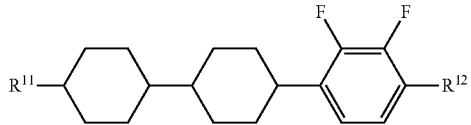

(2-6)

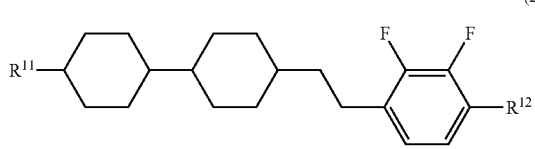

(2-7)

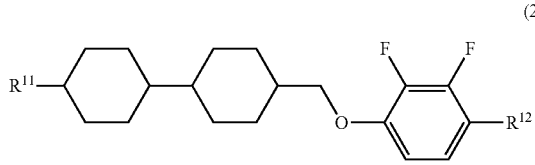

(2-8)

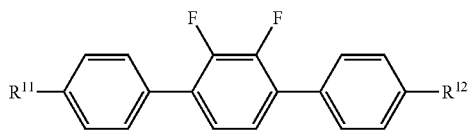

(2-9)

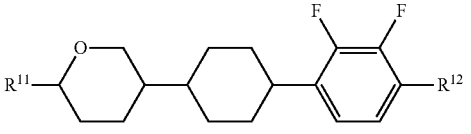

(2-10)

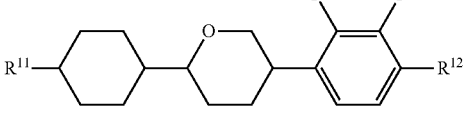

(2-11)

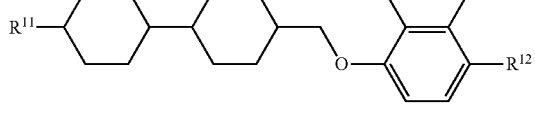

(2-12)

-continued

(2-13)

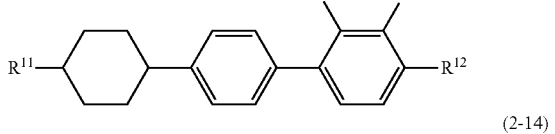
(2-14)

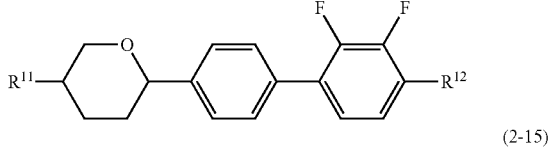
(2-15)

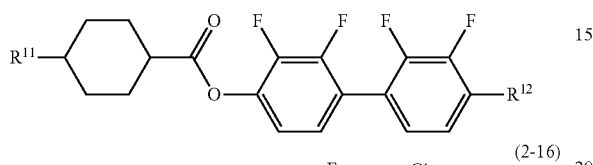
(2-16)

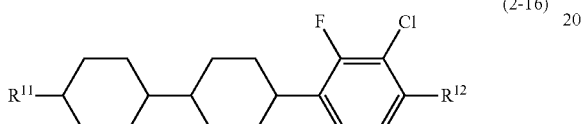
(2-17)

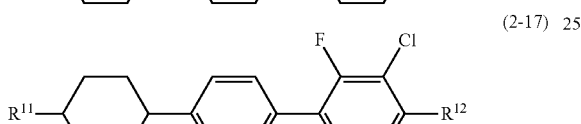
(2-18)

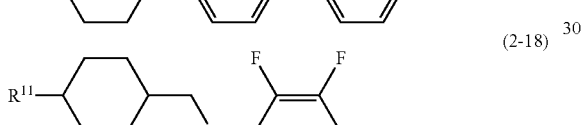
(2-19)

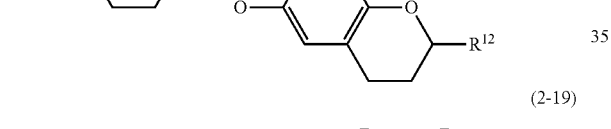

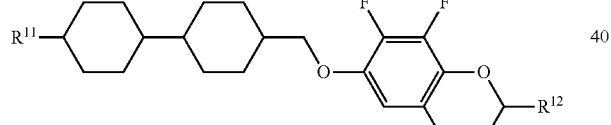

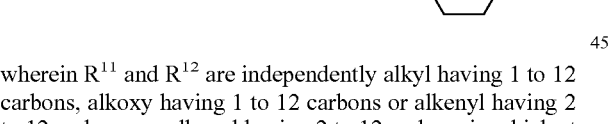

wherein $R^{11}$ and $R^{12}$ are independently alkyl having 1 to 12 carbons, alkoxy having 1 to 12 carbons or alkenyl having 2 to 12 carbons, or alkenyl having 2 to 12 carbons in which at least one of hydrogen is replaced by fluorine.

6. The liquid crystal composition according to claim 1, wherein a ratio of the second component is in the range of 10% by weight to 90% by weight based on the weight of a liquid crystal composition excluding the first component.

7. The liquid crystal composition according to claim 1, further containing at least one compound selected from the group of compounds represented by formula (3) as a third component:

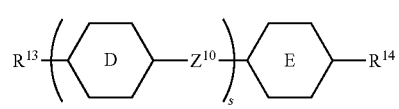
(3)

wherein $R^{13}$ and $R^{14}$ are independently alkyl having 1 to 12 carbons, alkoxy having 1 to 12 carbons or alkenyl having 2 to 12 carbons, or alkenyl having 2 to 12 carbons in which at least one of hydrogen was replaced by fluorine;

ring D and ring E are independently 1,4-cyclohexylene, 1,4-phenylene, 2-fluoro-1,4-phenylene, 3-fluoro-1,4-phenylene or 2,5-difluoro-1,4-phenylene;

$Z^{10}$ is independently a single bond, ethylene, methyleneoxy or carbonyloxy; and s is 1, 2 or 3.

8. The liquid crystal composition according to claim 7, wherein the third component is at least one compound selected from the group of compounds represented by formula (3-1) to formula (3-13):

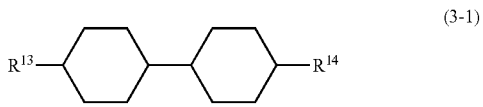
(3-1)

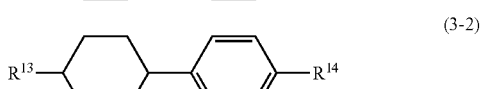
(3-2)

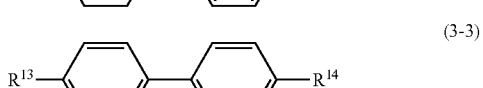
(3-3)

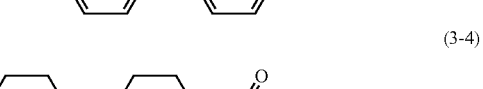
(3-4)

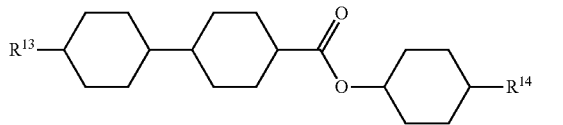
(3-5)

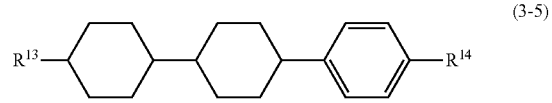
(3-6)

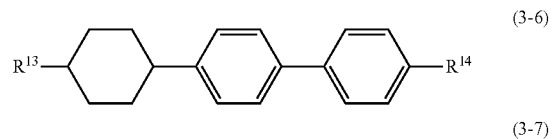
(3-7)

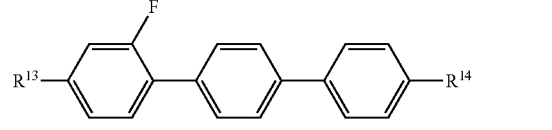
(3-8)

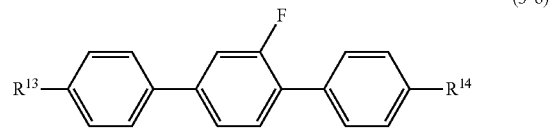
(3-9)

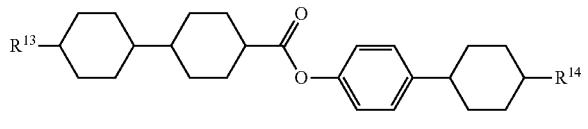
(3-10)

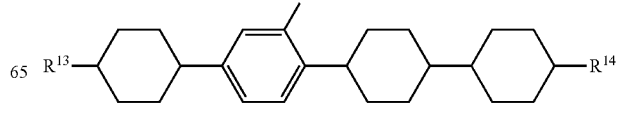

-continued (3-11)
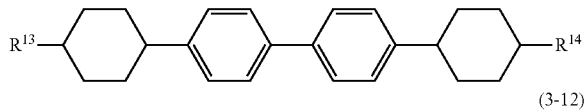

(3-12)
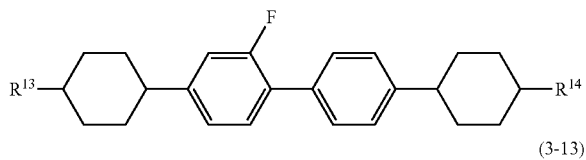

(3-13)
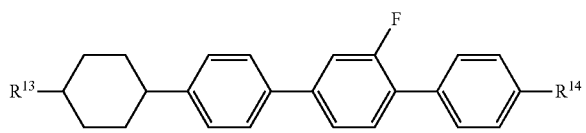

wherein $R^{13}$ and $R^{14}$ are independently alkyl having 1 to 12 carbons, alkoxy having 1 to 12 carbons or alkenyl having 2 to 12 carbons, or alkenyl having 2 to 12 carbons in which at least one of hydrogen is replaced by fluorine.

9. The liquid crystal composition according to claim 7, wherein a ratio of the third component is in the range of 10% by weight to 90% by weight based on the weight of a liquid crystal composition excluding the first component.

10. The liquid crystal composition according to claim 1, further containing a polymerization initiator.

11. The liquid crystal composition according to claim 1, further containing a polymerization inhibitor.

12. The liquid crystal composition according to claim 1, wherein a maximum temperature of a nematic phase is 70° C. or higher, and an optical anisotropy (25° C.) at a wavelength of 589 nanometers is 0.08 or more.

13. A liquid crystal display device, comprising two substrates having an electrode layer on at least one of the substrates, and arranging the liquid crystal composition according to claim 1 between the two substrates.

14. The liquid crystal display device according to claim 13, wherein an operating mode in the liquid crystal display device is a TN mode, a VA mode, an IPS mode or a PSA mode, and a driving mode in the liquid crystal display device is an active matrix mode.

* * * * *